United States Patent
Lee

(10) Patent No.: US 10,678,563 B2
(45) Date of Patent: Jun. 9, 2020

(54) DISPLAY APPARATUS AND METHOD FOR CONTROLLING DISPLAY APPARATUS

(71) Applicant: SAMSUNG ELECTRONICS CO., LTD., Suwon-si (KR)

(72) Inventor: Bo-ra Lee, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 15/802,103

(22) Filed: Nov. 2, 2017

(65) Prior Publication Data

US 2018/0129518 A1 May 10, 2018

(30) Foreign Application Priority Data

Nov. 2, 2016 (KR) .................. 10-2016-0145304

(51) Int. Cl.
| | |
|---|---|
| G06F 17/00 | (2019.01) |
| G06F 9/451 | (2018.01) |
| G06F 3/048 | (2013.01) |
| G06F 3/14 | (2006.01) |
| A61B 3/06 | (2006.01) |
| A61B 5/12 | (2006.01) |
| G06F 3/147 | (2006.01) |

(Continued)

(52) U.S. Cl.
CPC .............. *G06F 9/451* (2018.02); *A61B 3/066* (2013.01); *A61B 5/123* (2013.01); *G06F 3/048* (2013.01); *G06F 3/14* (2013.01); *G06F 3/147* (2013.01); *G06F 3/165* (2013.01); *G06F 3/167* (2013.01); *A61F 4/00* (2013.01); *G09G 2320/066* (2013.01); *G09G 2320/0693* (2013.01); *G09G 2340/04* (2013.01); *G09G 2340/14* (2013.01); *G09G 2354/00* (2013.01); *G09G 2380/08* (2013.01)

(58) Field of Classification Search
CPC ....................... G06F 3/167; G06F 2203/04806
See application file for complete search history.

(56) References Cited

U.S. PATENT DOCUMENTS

| | | | |
|---|---|---|---|
| 6,192,341 B1 * | 2/2001 | Becker ................ | G06F 3/04897 345/471 |
| 2004/0218451 A1 * | 11/2004 | Said ..................... | G06F 3/0481 365/222 |

(Continued)

FOREIGN PATENT DOCUMENTS

| | | |
|---|---|---|
| EP | 1 674 975 A2 | 6/2006 |
| EP | 2 796 993 A2 | 10/2014 |

(Continued)

OTHER PUBLICATIONS

Communication dated Jan. 29, 2018, issued by the European Patent Office in counterpart European application No. 17197163.3.

(Continued)

*Primary Examiner* — Andrew T McIntosh
(74) *Attorney, Agent, or Firm* — Sughrue Mion, PLLC

(57) ABSTRACT

A display apparatus and a method for controlling the display apparatus are provided. More specifically, the display apparatus outputs a visual test screen and an auditory test voice signal, determines a degree and a classification of impairment of a user, and sets a User Interface (UI) or sets a voice signal output based on the determined degree and classification of impairment.

15 Claims, 15 Drawing Sheets

(51) Int. Cl.
*G06F 3/16* (2006.01)
*A61F 4/00* (2006.01)

(56) References Cited

U.S. PATENT DOCUMENTS

| | | |
|---|---|---|
| 2010/0180238 A1 | 7/2010 | Lanfermann et al. |
| 2013/0120390 A1 | 5/2013 | Marchand et al. |
| 2013/0154937 A1 | 6/2013 | Park |
| 2014/0063071 A1* | 3/2014 | Leventhal ............ G06F 3/04812 345/661 |
| 2014/0240262 A1 | 8/2014 | Paul |
| 2014/0268060 A1* | 9/2014 | Lee ...................... A61B 3/0041 351/241 |
| 2014/0282285 A1* | 9/2014 | Sadhvani ............ G06F 3/04847 715/865 |
| 2015/0023535 A1* | 1/2015 | Shennib ................ H04R 25/70 381/314 |
| 2015/0199118 A1* | 7/2015 | Berger ................ G06F 3/04845 715/838 |
| 2016/0320935 A1 | 11/2016 | Shin et al. |
| 2017/0134821 A1* | 5/2017 | D'Amelio .......... H04N 21/4884 |

FOREIGN PATENT DOCUMENTS

| | | |
|---|---|---|
| KR | 1020130071253 A | 6/2013 |
| KR | 1020140025928 A | 3/2014 |
| KR | 1020140106801 A | 9/2014 |
| KR | 1020140127146 A | 11/2014 |
| WO | 2015/093636 A1 | 6/2015 |

OTHER PUBLICATIONS

Communication dated Nov. 6, 2018, issued by the European Patent Office in counterpart European Application No. 17197163.3.
Communication dated Aug. 16, 2019, issued by the European Patent Office in counterpart European Application No. 17197163.3.

* cited by examiner

FIG. 15

| DISABILITY CLASSIFICATION | AVAILABLE FUNCTIONS | |
|---|---|---|
| VISUAL DISABILITY (MILD) | -ENLARGE TEXT FEEDBACK SIZE SUCH AS MENU, CHANNEL, VOLUME<br>-ENLARGE SCREEN MAINLY FOCUSING ON MAJOR FIGURES<br>-HIGH-CONTRAST SCREEN<br>-ENLARGE VOICE FEEDBACK<br>-REMOTE CONTROLLER VIBRATION FEEDBACK<br>-SCREEN COMMENTARY FUNCTION | ~1501 |
| VISUAL DISABILITY (SEVERE) | -PROVIDE MENU, CHANNEL, VOLUME, ETC. THROUGH VOICE FEEDBACK<br>-PROVIDE ALL TEXT FEEDBACK THROUGH VOICE AS WELL<br>-VOICE FEEDBACK (IDENTIFY DEVICE LOCATION, DEVICE STATE CHANGE, ETC.)<br>-SCREEN COMMENTARY FUNCTION | ~1503 |
| HEARING DISABILITY (MILD) | -AUTOMATIC VOLUME INCREASE<br>-VIBRATION FEEDBACK (STATE CHANGE, NOTIFICATION, ETC.)<br>-AUTOMATIC SUBTITLE GENERATION FUNCTION | ~1505 |
| HEARING DISABILITY (SEVERE) | -ENLARGE SCREEN FOCUSING ON MAJOR FIGURES WHEN PLAYING IMAGE (SUPPORT LIP-READING)<br>-AUTOMATIC SUBTITLE GENERATION FUNCTION WHEN PLAYING IMAGE<br>-PROVIDE NOTIFICATION SUCH AS RINGTONE AND TEXT THROUGH VIBRATION AND SCREEN NOTIFICATION | ~1507 |
| READING DISABILITY (DYSLEXIA) | -ENLARGE TEXT FEEDBACK SIZE SUCH AS MENU, CHANNEL, VOLUME<br>-PROVIDE MENU, CHANNEL, VOLUME, ETC. THROUGH VOICE FEEDBACK<br>-CONVERT TEXT FEEDBACK INTO VOICE AND PROVIDE CONVERTED FEEDBACK | ~1509 |
| HEARING COMPREHENSION DISORDER (INTELLECTUAL DISABILITY) | -SPEED CONTROL OF VOICE FEEDBACK<br>-DESCRIBE MENU THROUGH VOICE | ~1511 |
| PHYSICAL DISABILITY | -REMOTE VOICE CONTROL<br>-NEAR-FIELD VOICE CONTROL | ~1513 |
| COLOR WEAKNESS DISABILITY | -COLOR WEAKNESS SCREEN CONVERSION FUNCTION | ~1515 |

DISPLAY APPARATUS AND METHOD FOR CONTROLLING DISPLAY APPARATUS

CROSS-REFERENCE TO RELATED APPLICATIONS

This application claims priority from Korean Patent Application No. 10-2016-0145304, filed on Nov. 2, 2016, in the Korean Intellectual Property Office, the disclosure of which is incorporated herein by reference in its entirety.

BACKGROUND

1. Field

Devices and methods consistent with the present disclosure relate to a display apparatus and a method for controlling the display apparatus, and more particularly, to an apparatus which provides a User Interface (UI) and a voice signal output setting suitable for a user.

2. Description of the Related Art

A display device has a function of changing a UI screen. Conventionally, the UI provided at the time of manufacturing has been provided to a user irrespective of whether the user using the display device has disabilities or not. Generally, since the interface set at the time of manufacturing is provided on the basis of a non-disabled person, the disabled have to undergo various steps in order to change to a UI suitable for them through the UI provided in the display device.

SUMMARY

An aspect of exemplary embodiments relates to providing a user with a visual test screen and a voice signal for auditory test to determine the degree of the user's impairment and thereby providing a UI suitable to the user.

According to an exemplary embodiment, there is provided a display apparatus including an input unit configured to receive a user input, a speaker configured to output a voice signal, a display configured to display a content, and a controller configured to control the input unit and the display, and the controller performs at least one of an operation of controlling the display to display a visual test screen and an operation of controlling the speaker to output an auditory test voice signal, receives a user input while the at least one operation is performed, determines a degree and a classification of impairment of a user based on the user input, and sets a User Interface (UI) or sets a voice signal output based on the determined degree and classification of impairment of the user.

The controller may provide information regarding the set UI or the voice signal output as at least one of a visual feedback and an auditory feedback.

The UI setting may include changing at least one of size, color and high-contrast of a UI displayed on the display.

The operation of controlling to display the visual test screen may include an operation of controlling to change and display a size of an object displayed on the display sequentially.

The object may include an image including a face of a person, and the controller may control the display to display the face of the person at a center of a screen.

The visual test screen may include an image for color weakness test.

The operation of controlling to output the auditory test voice signal may include an operation of controlling to change and output at least one of volume, pitch and left/right balance of the voice signal.

The setting the voice signal output may include changing at least one of volume, pitch and left/right balance of the output voice signal.

According to an exemplary embodiment, there is provided a display apparatus including an input unit configured to receive a user input, a display configured to display a content, and a controller configured to control the input unit and the display, and the controller displays a plurality of visual test screens on the display sequentially, receives a user input to select at least one of the plurality of visual test screens, determines a degree of visual impairment of a user based on the user input, and activates a voice guidance function on a screen of the display or sets a User Interface (UI) using a setting value corresponding to the selected visual test screen based on the determined degree of visual impairment.

The controller may output a plurality of auditory test voice signals sequentially, receive a user input to select one of the plurality of auditory test voice signals, determine a degree of hearing impairment of a user based on the user input, and activate a subtitle guidance function regarding a function of the display apparatus or set a voice signal output using a setting value corresponding to the selected auditory test voice signal based on the determined degree of hearing impairment.

According to an exemplary embodiment, there is provided a method for controlling a display apparatus, comprising performing at least one of an operation of displaying a visual test screen on a display and an operation of outputting an auditory test voice signal through a speaker, receiving a user input while the at least one operation is performed, determining a degree and a classification of impairment of a user based on the user input, and setting a User Interface (UI) or setting a voice signal output based on the determined degree and classification of impairment.

The method further includes providing information regarding the set UI or the voice signal output as at least one of a visual feedback and an auditory feedback.

The UI setting may include changing at least one of size, color and high-contrast of UI displayed on the display.

The operation of displaying the visual test screen may include changing and displaying a size of an object displayed on the display sequentially.

The object may include an image including a face of a person, and the operation of displaying the visual test screen may include displaying the face of the person at a center of a screen.

The visual test screen may include an image for color weakness test.

The operation of outputting the auditory test voice signal may include changing and outputting at least one of volume, pitch and left/right balance of the voice signal.

The voice setting may include changing at least one of volume, pitch and left/right balance of the output voice signal.

According to an exemplary embodiment, there is provided a method for controlling a display apparatus, including displaying a plurality of visual test screens on the display sequentially, receiving a user input to select at least one of the plurality of visual test screens, determining a degree of visual impairment of a user based on the user input, and activating a voice guidance function on a screen where the display is provided or setting a User Interface (UI) using a setting value corresponding to the selected visual test screen based on the determined degree of visual impairment The method may further include outputting a plurality of auditory test voice signals sequentially, receiving a user input to select one of the plurality of auditory test voice signals, determining a degree of hearing impairment of a user based on the user input, and activating a subtitle guidance function regarding a function of the display apparatus or setting a voice signal output using a setting value corresponding to the selected auditory test voice signal based on the determined degree of hearing impairment.

The display apparatus according to an exemplary embodiment outputs a visual test screen and an auditory test voice signal, determines a degree and a classification of impairment of a user, and sets a UI or sets a voice signal output based on the determined degree and classification of impairment. Accordingly, the display apparatus may easily set a UI or voice signal output suitable for a user with disability.

BRIEF DESCRIPTION OF THE DRAWINGS

The above and/or other aspects of the present inventive concept will be more apparent by describing certain exemplary embodiments of the present inventive concept with reference to the accompanying drawings, in which:

FIG. 15 illustrates an example regarding a function which a display apparatus can support according to the degree and classification of impairment of a user in the display apparatus according to an exemplary embodiment.

DETAILED DESCRIPTION OF EXEMPLARY EMBODIMENTS

Figure 1:
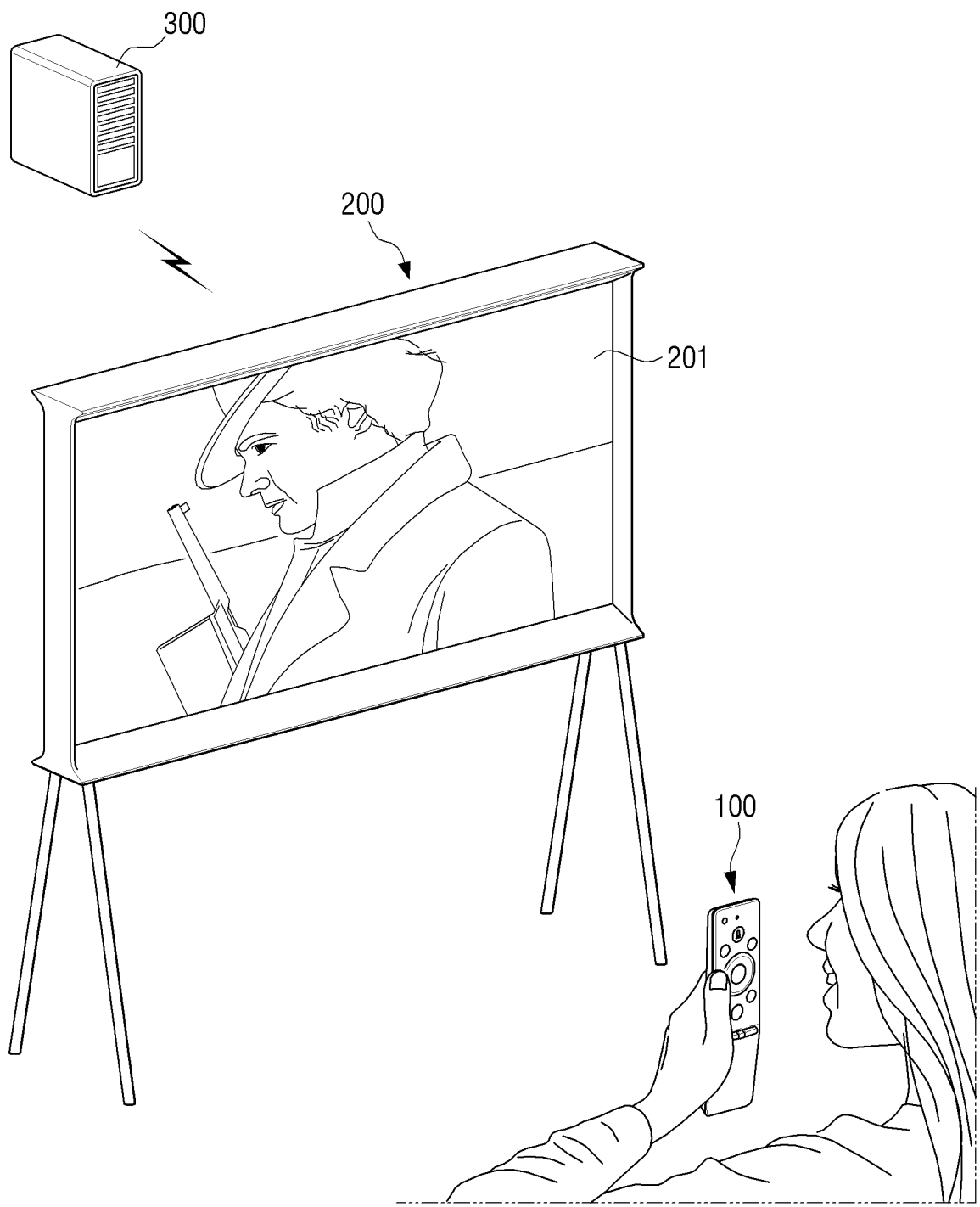
FIG. 1 is a schematic view illustrating an operation between a display apparatus, a remote controller and a server according to an exemplary embodiment.

Exemplary embodiments are described in greater detail with reference to the accompanying drawings. Exemplary embodiments of the present disclosure will now be described in greater detail with reference to the accompanying drawings. In the following description, same drawing reference numerals are used for the same elements even in different drawings.

Although the terms, 'first', 'second', etc. may be used herein to describe various elements, these elements should not be limited by these terms. The terms are used to distinguish one component from another component. For example, the 'first' component may be named the 'second' component, and vice versa, without departing from the scope of the present disclosure. As used herein, the term "and/or" includes any and all combinations of one or more of the associated listed items.

In an exemplary embodiment of the present disclosure, a "module" or a "unit" performs at least one function or operation, and may be implemented with hardware, software, or a combination of hardware and software. In addition, a plurality of "modules" or a plurality of "units" may be integrated into at least one module except for a "module" or a "unit" which has to be implemented with specific hardware, and may be implemented with at least one processor (not shown).

According to an exemplary embodiment, the "selecting of a key (or button)" of a remote controller (remote controller 100, refer to FIG. 1) may be used as a term for indicating pressing of the button (or key) or touching of the button (or key). Also, "user input" may be used as a term for indicating, for example, a user's selection of a button (or key), a user's pressing of a button (or key), a user's touching on a button, a user's touch gesture, a user's voice, or a user's motion.

In an exemplary embodiment, "a screen of a display apparatus" of a display apparatus may be used as a term including a display of the display apparatus.

In an exemplary embodiment, a User Interface (UI) may be used as a term including a graphic image, a graphic object, a still image, a moving image, and a text displayed on the screen of the display apparatus.

In addition, the UI may be to provide information to a user or to request for a user input.

In an exemplary embodiment, a voice signal may include an electrical signal or digital data generating a sound wave that can be heard by a person. In addition, a voice signal may include an electrical signal of an audible frequency band which can be heard by a person.

In an exemplary embodiment, the voice may refer to a sound wave that can be heard by a person, for example, directly to a human ear through a speaker.

The terms used in various exemplary embodiments are just for the purpose of describing exemplary embodiments, and are not intended to limit the present disclosure. Here, the singular forms are intended to include the plural forms as well, unless the context clearly indicates otherwise. In an exemplary embodiment, it should be understood that the term "comprise" or "include" as used herein refers to a presence of characteristic, number, step, operation, element, part, or a combination of these, but not to foreclose the existence of, or possibility of adding one or more of another characteristics, numbers, steps, operations, elements, parts or a combination of these.

In describing the drawings, the same reference numerals are used to refer to elements performing substantially the same functions.

FIG. 1 is a schematic view illustrating an operation between a display apparatus and an audio apparatus according to an exemplary embodiment.

FIG. 1 illustrates a display apparatus 200, a remote controller 100 and one or more servers 300.

Figure 2:
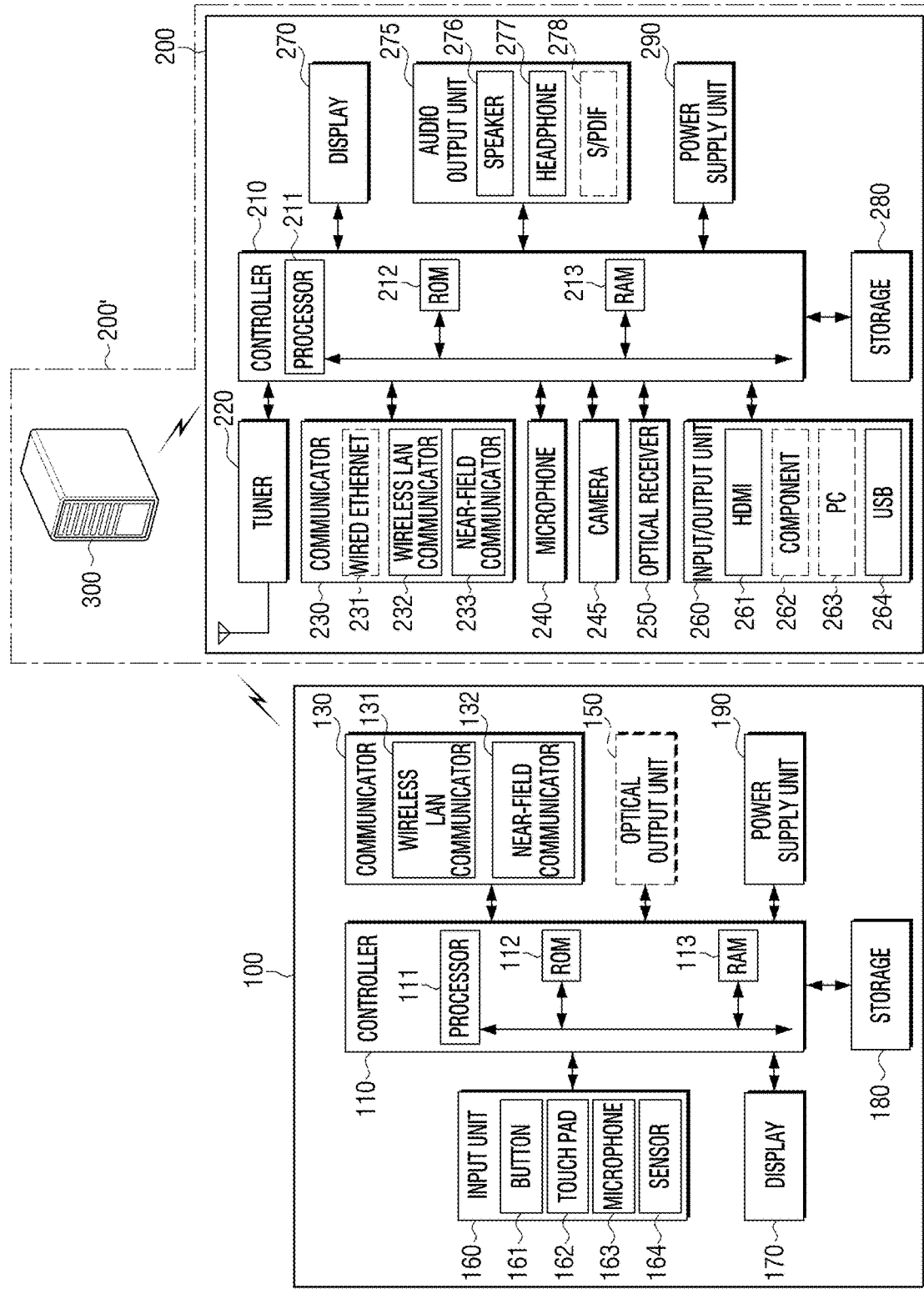
FIG. 2 is a block diagram illustrating a display apparatus, a remote controller and a server according to an exemplary embodiment.

The display apparatus 200 which includes a screen 201 and is capable of outputting not only a received broadcast but also a content may receive a user voice by using a built-in or connectable microphone 240 (refer to FIG. 2). The remote controller 100 may receive a user voice using a microphone 163 (refer to FIG. 2).

The remote controller 100 may control the display apparatus 200 by outputting (or transmitting) a control command through an infrared or near-field communication (for example, Bluetooth, etc.). In addition, the remote controller 100 may convert a voice received through an infrared or near-field communication (for example, Bluetooth, etc.) and transmit the converted voice to the display apparatus 200.

A user may control the display apparatus 200 (for example, power on/off, booting, channel change, volume adjustment, content playback, etc.) using voice recognition through selection of a key (or a button) on the remote controller 100, a user input (for example, a touch (gesture) through a touch pad) or motion recognition through a sensor 164 (refer to FIG. 2).

A user may control the display apparatus 200 using a voice. The microphone 163 of the remote controller 100 may receive a user voice corresponding to the control of the display apparatus 200. The remote controller 100 may convert the received voice into an electrical signal (for example, a digital signal, digital data or a packet) and transmit the converted voice to the display apparatus 200.

A user may control the functions of the display apparatus 200 (e.g., power on/off, booting, channel change, volume adjustment or content reproduction) with motion recognition through a camera 245 (refer to FIG. 2) attached on the display apparatus. In addition, the user may control the screen 201 of the display apparatus 200 using a movement of the remote controller 200 (for example, by gripping or moving the remote controller 200).

Referring to FIG. 2, the remote controller 100 includes a button 161 (or a key) corresponding to a function and/or a movement of the display apparatus 200. The button 161 may include a physical button or a touch button. Further, the remote controller 100 may include a single function button and/or a multifunction button corresponding to the functions performed in the display apparatus 200.

The single function button of the remote controller 100 (for example, power button and pointer key) may be used as a term which refers to a key corresponding to one of a plurality of functions performed in the display apparatus 200. The keys of the remote controller 100 may be single function keys in most cases.

The arrangement order and/or number of the buttons in the remote controller 100 may be added, changed or deleted depending on the functions of the display apparatus 200.

The server 300 may convert an electrical signal (or a packet corresponding to an electrical signal) corresponding to a user voice input in the remote controller 100 or the display apparatus 200 into voice data (for example, a text, a code, etc.) which is generated through voice recognition. In addition, the server 300 may include a machine learning, rule-based and dialog-based user intention analysis system in which a user's utterance is sued as a training set, and may recognize a user voice even if the user does not perform a predetermined type of utterance.

The interactive server (not shown) may convert the converted voice data into control information (for example, a control command controlling the display apparatus 100) which can be recognized in the display apparatus 200. The converted control information may be transmitted to the display apparatus 200.

FIG. 2 is a block diagram illustrating a display apparatus, a remote controller and a server according to an exemplary embodiment.

Referring to FIG. 2, the display apparatus 200 which receives an electrical signal corresponding to a user voice from the remote controller 100 may be connected to an external apparatus (for example, the server 300) in a wired or wireless manner by using a communicator 230 or an input/output unit 260.

The display apparatus 200 which receives an electrical signal corresponding to a user voice from the remote controller 100 may transmit an electrical signal (or a packet corresponding to an electrical signal) which is received using the communicator 230 or the input/output unit 260 to an external apparatus (for example, the server 300, etc.) connected in a wired or wireless manner. In addition, the display apparatus 200 may an electrical signal (or a packet corresponding to an electrical signal) corresponding to a user voice received through the microphone 240 to an external apparatus (for example, the server 300) connected via cable or wirelessly using the communicator 230 or the input/output unit 260. The external apparatus may include a portable phone (not shown), a smart phone (not shown), a tablet PC (not shown), and a PC (not shown).

The display apparatus 200 may include a display 270, and may further include one of a tuner 220, the communicator 230 and the input/output unit 260. The display apparatus 200 may include the display 270 and combination of the tuner 220, the communicator 230 and the input/output unit 260. Further, the display apparatus 200 having the display 270 may be electrically connected to a separate display apparatus (not shown) including a tuner (not shown).

The display apparatus 200 may be implemented to be, for example, analog TV, digital TV, 3D-TV, smart TV, LED TV, OLED TV, plasma TV, monitor, curved TV having the fixed curvature of the screen, flexible TV having the fixed curvature of the screen, bended TV having the fixed curvature of the screen, and/or curvature modifiable TV in which the curvature of the current screen can be modified by the received user input. However, the fact that it may not be limited to the above would be easily understood by those skilled in the art.

The display apparatus 200 includes the tuner 220, the communicator 230, the microphone 240, the camera 245, an optical receiver 250, the input/output unit 260, the display 270, an audio output unit 275, a storage 280 and a power supply unit 290. The display apparatus 200 may include a sensor which detects the internal state or the external state of the display apparatus 200 (for example, illumination sensor and temperature sensor, etc., not shown).

The controller 210 may include a processor 211, ROM 212 (or non-volatile memory) storing a control program for the controlling of the display apparatus 200, and RAM 213 (or volatile memory) for storing signals or data inputted outside the display apparatus 200 or for storing various jobs performed by the display apparatus 200.

The controller 210 controls general operations of the display apparatus 200 and signal flows between the internal elements 210-290 of the display apparatus 200, and processes data. The controller 210 controls power provided to internal elements 210 to 280 from the power supply unit 290. Further, when a user input is performed or previously established and when a stored condition is met, the controller 210 may execute Operation System (OS) or various applications stored in the storage 280.

The processor 211 may further include a graphic processing unit (GPU) for the graphic processing corresponding to an image or a video. The processor 211 may include a graphic processor (not shown) or may be provided separately from a graphic processor. The processor 211 may be implemented as a System On Chip (SoC) including a core (not shown) and GPU (not shown). In addition, the processor 211 may be implemented as a SoC including at least one of the ROM 212 and the RAM 213. The processor 211 may include a single core, a dual core, a triple core, a quad core, or a larger number of the cores.

The processor 211 of the display apparatus 200 may include a plurality of processors. The plurality of processors may include a main processor (not shown) and a sub processor (not shown) which operates in a screen-off (or power-off) mode and/or a ready mode which is one of the states of the display apparatus 200. The plurality of sensors may further include a censor processor (not shown) for controlling a sensor (not shown).

The processor 211, ROM 212 and RAM 213 may be connected to each other through an internal bus.

In this exemplary embodiment, the term, "controller of the display apparatus 200", may include the processor 211, the ROM 212 and the RAM 213 of the display apparatus 200. In this exemplary embodiment, the term, "controller of the display apparatus 200", may refer to the processor 211 of the display apparatus 200. In addition, in this exemplary embodiment, the term, "controller of the display apparatus 200" may include the main processor and the sub processor of the display apparatus 200, the ROM 212, and the RAM 213.

The fact that the configuration and the operations of the controller 210 may be variously implemented according to an embodiment can be understood easily by those skilled in the art.

The tuner 220 may tune and select only the channel frequency to be received from the display apparatus 200 among various wave components through the amplification, mixing, resonance, etc. of the broadcast signal received via cable or wirelessly. The broadcast signal includes a video, an audio, and additional data (for example, Electronic Program Guide (EPG)).

The tuner 220 may receive a video, an audio and data on the frequency bandwidth corresponding to a channel number (for example, cable broadcast channel No. 506) in response to the user input (for example, a voice, a motion, a button input, a touch input, etc.).

The tuner 220 may receive a broadcast signal from various sources such as terrestrial broadcasting, cable broadcasting, satellite broadcasting, Internet broadcasting, etc.

The tuner 220 may be implemented to be all-in-one with the display apparatus 200, a tuner (not shown) electrically connected to the display apparatus 200, or a separate display apparatus (not shown, for example, a set-top box or a one connect).

The communicator 230 may connect the display apparatus 200 to the remote controller 100 or an external apparatus under the control of the controller 210. The communicator 230 may transmit an electrical signal (or a packet corresponding to an electrical signal) corresponding to a user voice to the server 300 or receive voice data corresponding to an electrical signal (or a packet corresponding to an electrical signal) from the server 300 under the control of the controller 210.

The communicator 230 may include at least one of a wired Ethernet 231, a wireless LAN communicator 232 and a near-field communicator 233 in accordance with the performance and structure of the display apparatus 200. In addition, the communicator 230 may include combination of the Ethernet 231, the wireless LAN communicator 232 and the near-field communicator 233.

The wireless LAN communicator 232 may be wirelessly connected to an access point (AP) under the control of the controller 210 at a place where the AP is established. For example, the wireless LAN communicator 232 may include Wi-Fi. The wireless LAN communicator 232 may support the wireless LAN standard (IEEE802.11x) of the Institute of Electrical and Electronic Engineers (IEEE). Further, the near field communicator 233 may perform the near field communication between the remote controller 100 and an external apparatus without an AP under the control of the controller 210. The near field communication, for example, may include Bluetooth, Bluetooth low energy, infrared data association (IrDA), ultra wideband (UWB), or near field communication (NFC), etc.

The communicator 230 according to an exemplary embodiment may receive a control signal transmitted from the remote controller 100. Further, the near field communicator 233 may receive a control signal transmitted from the remote controller 100 under the control of the controller 210.

The microphone 240 receives a voice uttered by a user. The microphone 240 may convert the received voice into an electrical signal and output the electrical signal to the controller 210. The user voice, for example, may be a voice corresponding to a user guide, a menu or a function control of the display apparatus 200. The recognition range of the microphone 240 may vary depending on the size of a user voice and a surrounding environment (for example, speaker sound and ambient noise).

The microphone 240 may be implemented integrally with or separated from the display apparatus 200. The separate microphone 240 may be electrically connected to the display apparatus 200 through the communicator 230 or the input/output unit 260.

The camera 245 photographs a video (for example, consecutive frames) corresponding to a user motion within the recognition range of the camera. The user motion, for example, may include the presence of the user (for example, if the user appears within the recognition range of the camera), the user's body part such as face, look, hand, fist, and finger or a motion of the user's body part. The camera 245 may consist of a lens (not shown) and an image sensor (not shown).

The camera 245 may be located at one of the top, bottom, left and right sides of the display apparatus 200.

The camera 245 may convert the consecutive frames photographed under the control of the controller 210 and output the converted frames to the controller 210. The controller 210 may recognize a user motion by analyzing the photographed consecutive frames. The controller 210 may use the result of motion recognition to display a guide or a menu on the display apparatus 200 or perform a control operation (for example, channel change, volume control, etc.).

If there are a plurality of cameras 245, a three-dimensional still image or a three-dimensional motion (or an image) may be received.

The camera 245 may be separated from the display apparatus 200 or embedded in the display apparatus 200. The electronic apparatus (not shown) including a separate camera (not shown) may be electrically connected to the display apparatus 200 through the communicator 230 or the input/output unit 260.

The optical receiver 250 receives an optical signal (including a control signal) outputted from the remote controller 100 through an optical window (not shown).

The optical receiver 250 may receive an optical signal corresponding to a user input (for example, touching, pressing, touch gestures, voice or motion) from the remote controller 200. A control signal may be acquired from the received optical signal. The received optical signal and/or the acquired control signal may be transmitted to the controller 210.

The input/output unit 260 receives a content from the outside of the display apparatus 200 under the control of the controller 210. The content may include a video, an image, a text or a web document, for example.

The input/output unit 260 may include one of a high-definition multimedia interface port (HDMI) 261, a component inputting jack 262, a PC inputting port 263, and a USB inputting jack 264 corresponding to the reception of the content. The input/output unit 260 may include combination of HDMI inputting port 261, the component inputting jack 262, the PC inputting port 263, and the USB inputting jack 264. The input/output unit 260 may be added, removed and/or changed according to the performance and structure of the display apparatus 200, which can be easily understood by those skilled in the art.

The display 270 displays a video included in a broadcast signal received through the tuner 220 under the control of the controller 210. The display 270 may display a content (for example, a video) which is inputted through the communicator 230 or the input/output unit 260. The display 270 may output a content stored in the storage 280 under the control of the controller 210. In addition, the display 270 may display a user interface for performing a voice recognition task corresponding to voice recognition or a user interface for performing a motion recognition task corresponding to voice recognition. For example, the user interface may include a voice command guide (for example, recommended voice data or recommended guide) and a motion command guide.

The screen 201 of the display apparatus 200 according to an exemplary embodiment may be used to include the display 270 of the display apparatus 200.

The display 270 according to an exemplary embodiment may display a visual feedback corresponding to the display of a recommended guide under the control of the controller 210.

The display 270 according to another exemplary embodiment may be separated from the display apparatus 200. The display 270 may electrically connected to the display apparatus 200 through the input/output unit 260 of the display apparatus 200.

The audio output unit 275 outputs an audio included in the broadcast signal received through the tuner 220 under the control of the controller 210. The audio output unit 275 may output an audio (for example, an audio corresponding to a voice or sound) inputted through the communicator 230 or the input/output unit 260. Further, the audio output unit 275 may output an audio file stored in the storage 280 under the control of the controller 210.

The audio output unit 275 may include one of a speaker 276, a headphone output terminal 277 and S/PDIF output terminal 278. Further, the audio output unit 275 may include combination of the speaker 276, the headphone output unit 277 and S/PDIF output terminal 278.

The audio output unit 275 according to an exemplary embodiment may output an auditory feedback corresponding to information provided to a user under the control of the controller 210.

The storage 280 may store various data, programs and applications to drive and control the display apparatus 200 under the control of the controller 210. The storage 280 may store signals or data inputted/outputted in accordance with the operations of the tuner 220, the communicator 230, the microphone 240, the camera 245, the optical receiver 250, the input/output unit 260, the display 270, the audio output unit 275 and the power supply 290.

The storage 280 may store control programs to control the display apparatus 200 and the controller 210, applications initially provided by a manufacturer or downloaded externally, GUIs related with the applications, objects to provide GUIs (for example, images, texts, icons, buttons, etc.), user information, documents, voice database, motion database or related data.

The storage 280 may include broadcast reception module, channel control module, volume control module, communication control module, voice recognition module, motion recognition module, optical reception module, display control module, audio control module, external input control module, power control module, voice database, or motion database although not illustrated.

The modules and database which are not illustrated in the storage may be implemented in the form of software for performing a control function of broadcasting reception, a channel control function, a volume control function, a communication control function, a voice recognition function, a motion recognition function, an optical reception control function, a display control function, an audio control function, an external input control function, or a power control function of the display apparatus 200. The controller 210 may perform the operations and/or functions of the display apparatus 200 by using the software stored in the storage 280.

The storage 280 may store voice data received from the server 300. The storage 280 may store control information received from the server 300. The storage 280 may store control information received from an interactive server (not shown).

The storage 280 may store database corresponding to a phoneme which corresponds to a user voice. In addition, the storage 280 may store control information database corresponding to voice data.

The storage 280 may store a video, an image or a text corresponding to a visual feedback.

The storage 280 may store sound corresponding to an auditory feedback.

The storage 280 may store a feedback providing time (for example, 300 ms) of a feedback provided to a user.

In this exemplary embodiment, the term "storage" may be understood as a term including the storage 280, the ROM 212 and the RAM 213 of the controller 210, a storage (not illustrated) implemented to be SoC (not illustrated), a memory card (for example, a micro SD card and a USB card, not illustrated) attached to the display apparatus 200, or an external storage (for example, a USB memory, etc. not illustrated) connectable to the USB port 264 of the input/output unit 260. Further, the storage may include a non-volatile memory, a volatile memory, a hard disk drive (HDD) or a solid state drive (SDD).

The power supply 290 provides power input from an external power source to the internal elements 210-280 of the display apparatus 200 under the control of the controller 210. The power supply unit 290 may supply power which is input from one or more batteries (not illustrated) positioned within the display apparatus 200 to the internal elements 210 to 280 under the control of the controller 210.

The power supply unit 290 may include a battery (not shown) for providing power to the camera 245 of the display apparatus 200 in which the display apparatus 200 is turned off, but its power plug is connected to a power outlet.

Some of the elements (for example, 210-290) illustrated in in the display apparatus 200 of FIGS. 1 and 2 may be added, changed, or deleted (for example, at least one of the boxes illustrated with dotted lines) according to the performance and/or type of the display apparatus 200. Further, the positions of the elements (for example, 210-290) may be modified according to the performance or structure of the display apparatus 200, which can be readily understood by those skilled in the related art.

Referring to FIG. 2, the remote controller 100 which controls the display apparatus 200 remotely includes the controller 110, the communicator 130, the input unit 160, the optical output unit 150, the display 170, the storage 180, and the power supply unit 190. The remote controller 100 may include one of the communicator 130 and the optical output unit 150. In addition, the remote controller 110 may include both the communicator 130 and the optical output unit 150.

The term "remote controller" may be used to refer to an apparatus which is capable of controlling the display apparatus 200 remotely. Further, the remote controller 100 may include an apparatus in which an application (not shown) for controlling the display apparatus 200 can be installed (or can be downloaded from outside).

The apparatus in which an application (not shown) for controlling the display apparatus 200 is installed may have a display (for example, a display having only a display panel without a touch screen or a touch panel). For example, the apparatus having a display may include a mobile phone (not shown), a smart phone (not shown), a tablet PC (not shown), a notebook PC (not shown), and another display apparatus (not shown), or home appliances (for example, a refrigerator, washing machine, cleaner, etc.).

A user may control the display apparatus 200 by using the function button (for example, a button for switching channels) in the graphic user interface (GUI) provided by the application which is executed.

The controller 110 may include a processor 111, a ROM 112 (or non-volatile memory) storing a control program for controlling the remote controller 100, and a RAM 113 (or volatile memory) storing signals or data inputted externally from the remote controller 100 or being used as a storage area for various operations performed in the remote controller 100.

The controller 110 controls the overall operations of the remote controller 100 and signal flows between the internal elements 110-190, and processes data. The controller 110 controls power supply of internal elements 110-180 using the power supply unit 190.

According to an exemplary embodiment, the term, 'controller 110' may include the processor 111, the ROM 112 and the RAM 113 of the remote controller 100.

The communicator 130, under the control of the controller 110, may transmit a control signal (for example, a control signal corresponding to power-on, a control signal corresponding to volume control, etc.) corresponding to a user input (for example, touching, pressing, touch gestures, voice or motion) to the display apparatus 200 to be controlled.

The communicator 130 may be wirelessly connected to the display apparatus 200 under the control of the controller 110. The communicator 130 may include at least one or both of a wireless local area network (LAN) communicator 131 and a near field communicator 132.

The communicator 130 of the remote controller 100 is substantially similar to the communicator 230 of the display apparatus 200 and thus, the overlapping description will not be provided.

The input unit 160 may include a button 161 or a touch pad 162 which receives a user input (for example, touching or pressing) to control the display apparatus 200. The input/output unit 160 may include a microphone 163 receiving the uttered user voice, a sensor 164 detecting the movement of the remote controller 100 or a vibration motor (not shown) providing a haptic feedback.

The input/output unit 160 may output an electrical signal (for example, an analog signal or a digital signal) corresponding to the received user input (for example, touching, pressing, touch gestures, voice or motion) to the controller 110.

The button 161 may receive a user input. The touch pad 162 may receive a user touch or a user touch gesture. The touch pad 162 may be implemented as a direction key and an enter key. In addition, the touch pad 162 may be located at the front side of the remote controller 100.

The microphone 163 receives a user's uttered voice. The microphone 163 may convert the received user voice and output the converted voice to the controller 110. The controller 110 may generate a control signal (or an electrical signal) corresponding to the user voice and transmit the generated signal to the display apparatus 200 through the communicator 130.

The sensor 164 may detect the internal state and/or the external state of the remote controller 100. For example, the sensor 164 may include a motion sensor (not shown), a gyro sensor (not shown), an acceleration sensor (not shown), or a gravity sensor (not shown). The sensor 164 may respectively measure the motion acceleration or the gravity acceleration of the remote controller 100.

A vibration motor (not shown) may convert an electrical signal into a mechanical vibration under the control of the controller 110. For example, the vibration motor (not shown) may include a linear vibration motor, a bar type vibration motor, a coin type vibration motor or a piezo vibration motor. The vibration motor (not shown) may be one or plural positioned within the remote controller 100.

The optical output unit 150 outputs an optical signal (for example, a control signal) corresponding to a user input (for example, touching, pressing, touch gestures, voice or motion) under the control of the controller 110. The output optical signal may be received in the optical receiver 250 of the display apparatus 200. For the remote controller code format used in the remote controller 100, one of the manufacturer-exclusive remote controller code format and the commercial remote controller code format may be used. The remote controller code format may include the leader code and the data word. The outputted optical signal may be modulated with the carrier wave and outputted. The control signal may be stored in the storage 180 or generated by the controller 110. The remote controller 100 may include Infrared-laser emitting diode (IR-LED).

The remote controller 100 may include at least one or both of the communicator 130 and the optical output unit 150 which are capable of transmitting a control signal to the display apparatus 200.

The controller 110 may output a control signal corresponding to a user voice to the display apparatus 200 through at least one of the communicator 130 and the optical output unit 150. The controller 110 may transmit a control signal corresponding to a user voice preferentially to the display apparatus 200 through one of the communicator 130 and the optical output unit 150 (for example, the communicator 130).

The display 170 may display a channel number and channel name of a broadcast displayed on the display apparatus 200 and/or the state of the display apparatus (for example, screen off, ready mode, welcome mode and/or general mode), etc.

If an optical signal is output from the remote controller 100 to the display apparatus 200, the display 170 may display "TV on" for turning on the display apparatus 200 under the control of the controller 110, "TV off" for turning off the display apparatus 200, "Ch No." for displaying a selected channel number, or a text, an icon or a symbol corresponding to "Vol value" for representing an adjusted volume.

The display 170 may, for example, include a display using a liquid crystal display (LCD) method, an organic light emitting diodes (OLED) method or vacuum fluorescent display (VFD) method.

The storage 180 may store various data, programs or applications for driving and controlling the remote controller 100 under the control of the controller 110. The storage 180 may store signals or data inputted or outputted for driving the communicator 130, the optical output unit 150 and the power supply unit 190.

The storage 180 may store control information corresponding to a user input (for example, touching, pressing, touch gestures, voice or motion) received under the control of the controller 110 and/or control information corresponding to the movement of the remote controller 100.

The storage 180 may store remote controller information corresponding to the remote controller 100. The remote controller information may include a model name, an original device ID, the remaining memory amount, whether there is object data or not, Bluetooth version or Bluetooth profile.

The power supply unit 190 may provide power to the elements 110-180 of the remote controller 100 under the control of the controller 110. The power supply unit 190 may provide power to the elements 110-180 from one or more batteries positioned in the remote controller 100. The battery may be positioned inside the space between the surface of the remote controller 100 (for example, where the button 161 or the touch pad 162 is positioned) and the rear surface (not shown) of the remote controller 100.

At least one of the elements illustrated in the remote controller 100 of FIGS. 1 and 2 may be added or deleted (for example, at least one of the boxes illustrated with dotted lines) according to the performance of the remote controller 100. In addition, the positions of the elements may be changed according to the performance or structure of the remote controller 100, which can be easily understood by those skilled in the art.

The server 300 (or a voice recognition server) receives a packet corresponding to the user voice input in the remote controller 100 or the display apparatus 200 through a communicator (not shown). The controller (not shown) of the server 300 performs voice recognition by analyzing the received packet using a voice recognition unit (not shown) and a voice recognition algorithm.

The controller (not shown) of the server 300 may convert an electrical signal (or a packet corresponding to an electrical signal) which is received into voice recognition data including a word or a text in the form of sentence using a voice recognition algorithm.

The controller (not shown) of the server 300 may transmit voice data to the display apparatus 200 through a communicator (not shown).

The controller (not shown) of the server 300 may convert voice data into control information (for example, a control command). The control information may control the operation (or function) of the display apparatus 200.

The server 300 may include control information database. The controller (not shown) of the server 300 may determine control information corresponding to converted voice data using the stored control information database.

The server 300 may convert the converted voice data into control information (for example, parsing by the controller 210 of the display apparatus 200) for controlling the display apparatus 200 using the control information database.

The controller (not shown) of the server 300 may transmit the control information to the display apparatus 200 through a communicator (not shown).

In this exemplary embodiment, the server 300 may be provided integrally with the display apparatus 200 (200'). The server 300 may be included in the display apparatus 200 as a separate element from the elements 210 to 290 of the display apparatus 200. The server 300 may be embedded in the storage 280 of the display apparatus 200 or provided in a separate storage (not shown).

In this exemplary embodiment, an interactive server (not shown) may be implemented separately from the server 300. The interactive server (not shown) may convert voice data which is converted in the server 300 into control information. The interactive server (not shown) may convert voice data received from one of the server 300 and the display apparatus 200 into control information. The interactive server (not shown) may transmit the converted control information to the display apparatus 200.

At least one of the elements illustrated in the server 300 of FIGS. 1 and 2 may be added or deleted according to the performance of the server 300.

Figure 3:
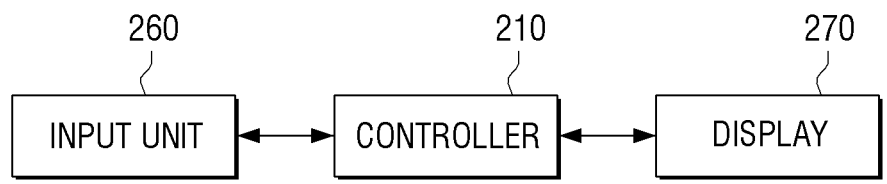
FIG. 3 is a block diagram of a display apparatus according to an exemplary embodiment.

FIG. 3 is a block diagram illustrating a display apparatus according to an exemplary embodiment.

Referring to FIG. 3, the display apparatus 200 may include the input unit 260, the display 270 and the controller 210.

The input unit 260 may receive a user input. For example, if a user presses a button provided on the remote controller 100, make an utterance, or takes a specific motion, the input unit 260 may receive a user input.

The display 270 may display a content on a screen. The content may include a moving image, a still image, a web page, and a UI.

The controller 210 may control the input unit 260 and the display 270.

The controller 210 may perform at least one of an operation of controlling the display 270 to display a visual test screen and an operation of outputting an audio signal for auditory test, receive a user input while the operation is performed, determine a degree of disability of the user and a disability classification based on the user input, and set a UI based on the determined degree of disability and the disability classification or set a voice signal output.

In addition, the controller 210 may provide information regarding the set UI or voice signal output through at least one of a visual feedback and an auditory feedback.

Here, setting the UI may be to change at least one of the size, color and high-contrast of the UI.

The operation of displaying a visual test screen may be an operation of changing the size of the object included in the screen sequentially and displaying the object.

For example, the controller 210 may control the display 270 to display a screen in which the size of the object displayed in the display 270 changes sequentially.

The controller 210 may display the size of the object small on the first screen, middle on the second screen and large on the third screen. Meanwhile, according to an exemplary embodiment, the object size may be displayed step by step by dividing into more steps than three steps.

While the screen in which the size of the object on the display 270 changes sequentially is displayed, the controller 210 may receive a user input and control the display to change at least one of the size, color and high-contrast of the UI based on the received user input.

For example, if a user input is received while the first screen is displayed on the display 270, the controller 210 may set the size of the UI to be small.

If a user input is received while the second screen is displayed on the display 270, the controller 210 may set the size of the UI to be middle. If a user input is received while the third screen is displayed on the display 270, the controller 210 may set the size of the UI to be large.

The object may include an image including a face of a person, and the controller 210 may control the display 270 to display the face of the person at the center of the screen.

The controller 210 may display an image including a face of a person on the screen and request the user to input a screen that the user feels comfortable while enlarging the image sequentially. Accordingly, if the user selects a screen which the user feels comfortable, the size of the UI may be changed to a setting value corresponding to the selected screen.

The visual test screen may include an image for color weakness test.

The controller 210 may sequentially display a screen including the color weakness test image while requesting a user input. For example, the controller 210 may display a screen for identifying a person with green color weakness on the first screen, a screen for identifying a person with blue color weakness on the second screen and a screen for identifying a person with red color weakness on the third screen while requesting the user to select a screen that can be identified. If the user selects the first screen, the controller 210 may set the color of the UI to a color that excludes green color. If the user selects the second screen, the controller 210 may set the color of the UI to a color that excludes blue color. If the user selects the third screen, the controller 210 may set the color of the UI to a color that excludes red color.

Meanwhile, the controller 210 may perform the operation of outputting a voice signal for auditory test. The operation of outputting a voice signal for auditory test may be changing one of the volume, pitch and left-right balance of the voice signal sequentially and outputting the voice signal. Here, the operation of "outputting a voice signal" may refer to that the controller 210 transmits an electrical signal or voice data corresponding to the voice through a voice signal output device (for example, a speaker).

The voice signal may include a general human voice or music. The controller 210 may output a message for requesting a user input, but may receive a user input by changing and outputting the volume sequentially. The controller 210 may output a message for requesting a user input, but may receive a user input by changing and outputting the pitch sequentially. The controller 210 may output a message for requesting a user input, but may receive a user input by changing and outputting the left-right balance sequentially. In each case, when a user input is received, the controller 210 may determine the degree of auditory disability of the user according to the user input and set the voice signal output according to the determined degree of auditory disability of the user. When the voice signal output is set, it affects the voice signal which is output later, and at least one of the volume, pitch and left-right balance of the output voice signal may change as the voice signal output is set.

According to an exemplary embodiment, the controller 210 may display a plurality of visual test screens sequentially on the display, receive a user input to select one of the plurality of visual test screens, determine the degree of visual disability of the user based on the user input, and activate a voice guidance function on the screen or set the UI to a setting value corresponding to the selected visual test screen according to the determined degree of visual disability.

According to another exemplary embodiment, the controller 210 may output a plurality of auditory test voice signals sequentially, receive a user input to select one of the plurality of auditory test voice signals, determine the degree of auditory disability of the user based on the user input, and activate a subtitle guidance function regarding the function of the display apparatus or set the voice signal output to a setting value corresponding to the selected auditory test voice signal according to the determined degree of auditory disability.

Figure 4:
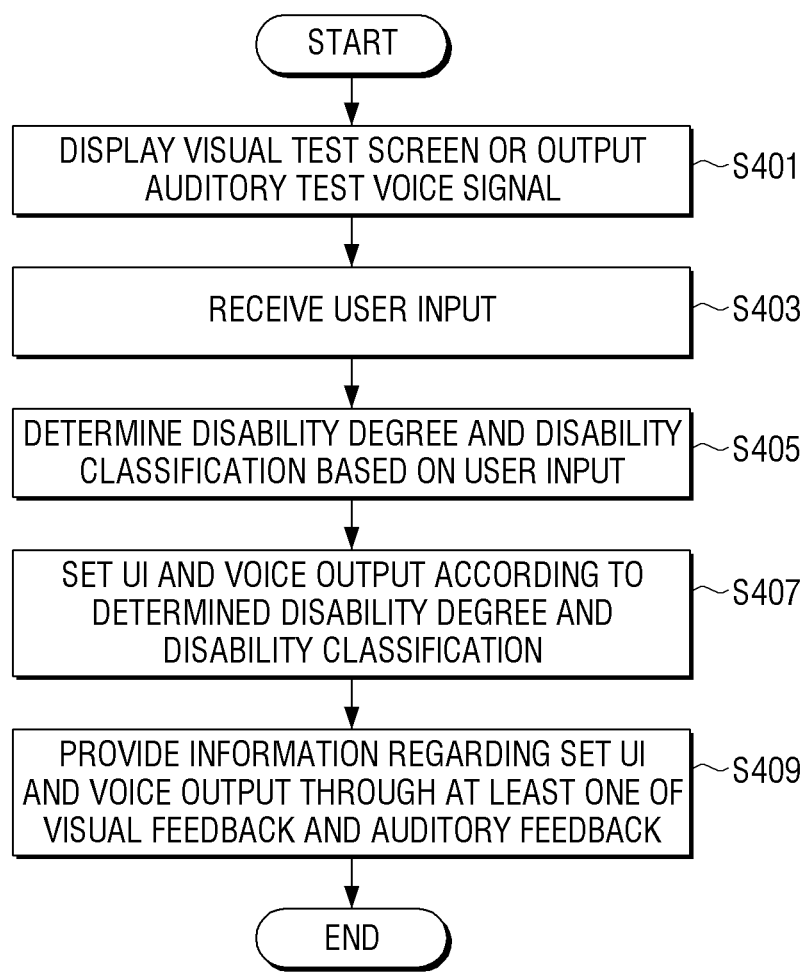
FIG. 4 is a view illustrating a process of setting a UI and outputting a voice signal according to a user input by a display apparatus according to an exemplary embodiment.

FIG. 4 illustrates a process in which a display apparatus sets a UI and voice signal output based on a user input according to an exemplary embodiment.

Figure 7:
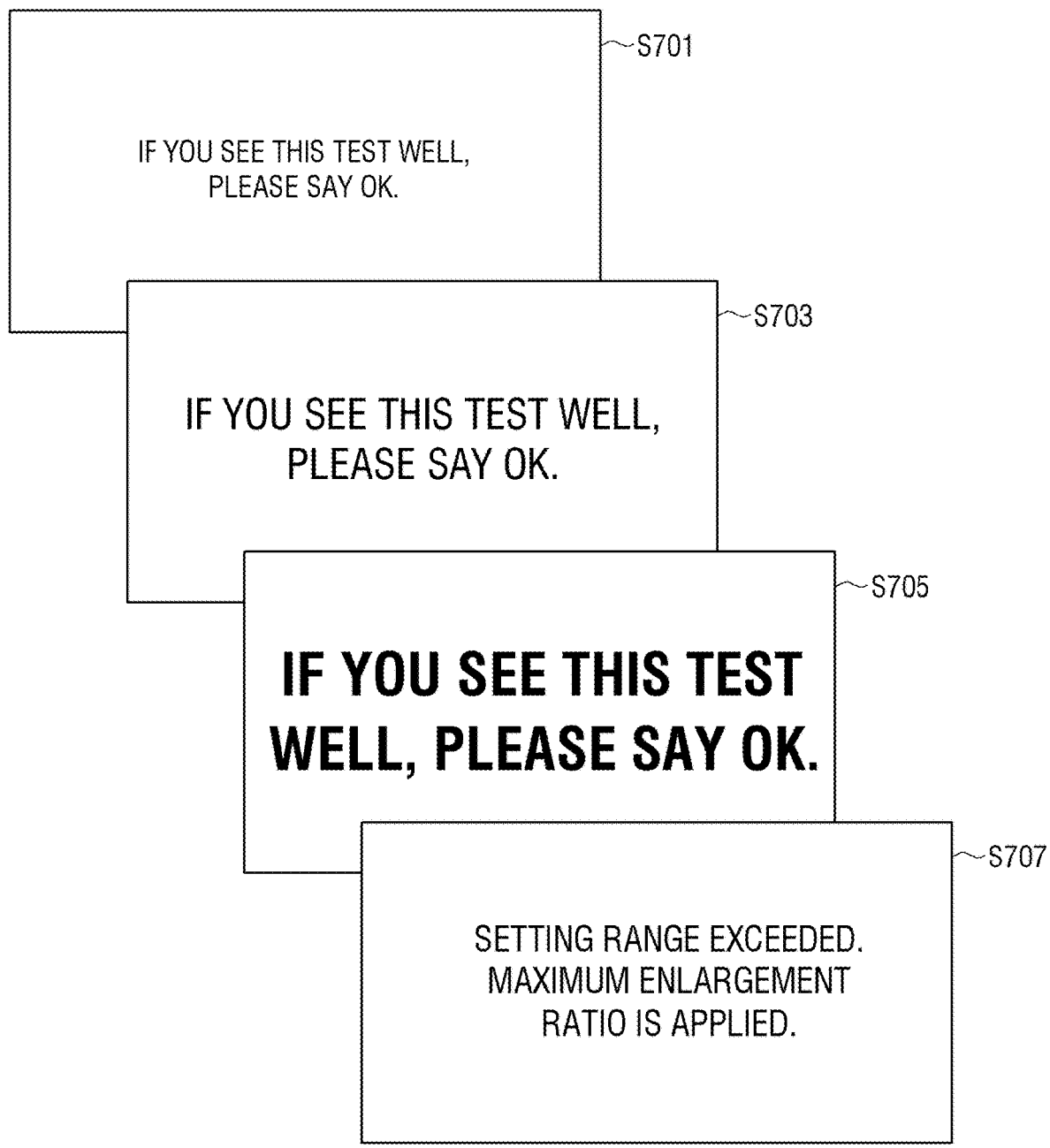
FIGS. 7 to 9 illustrate examples of a visual test screen according to an exemplary embodiment.
Figure 8:
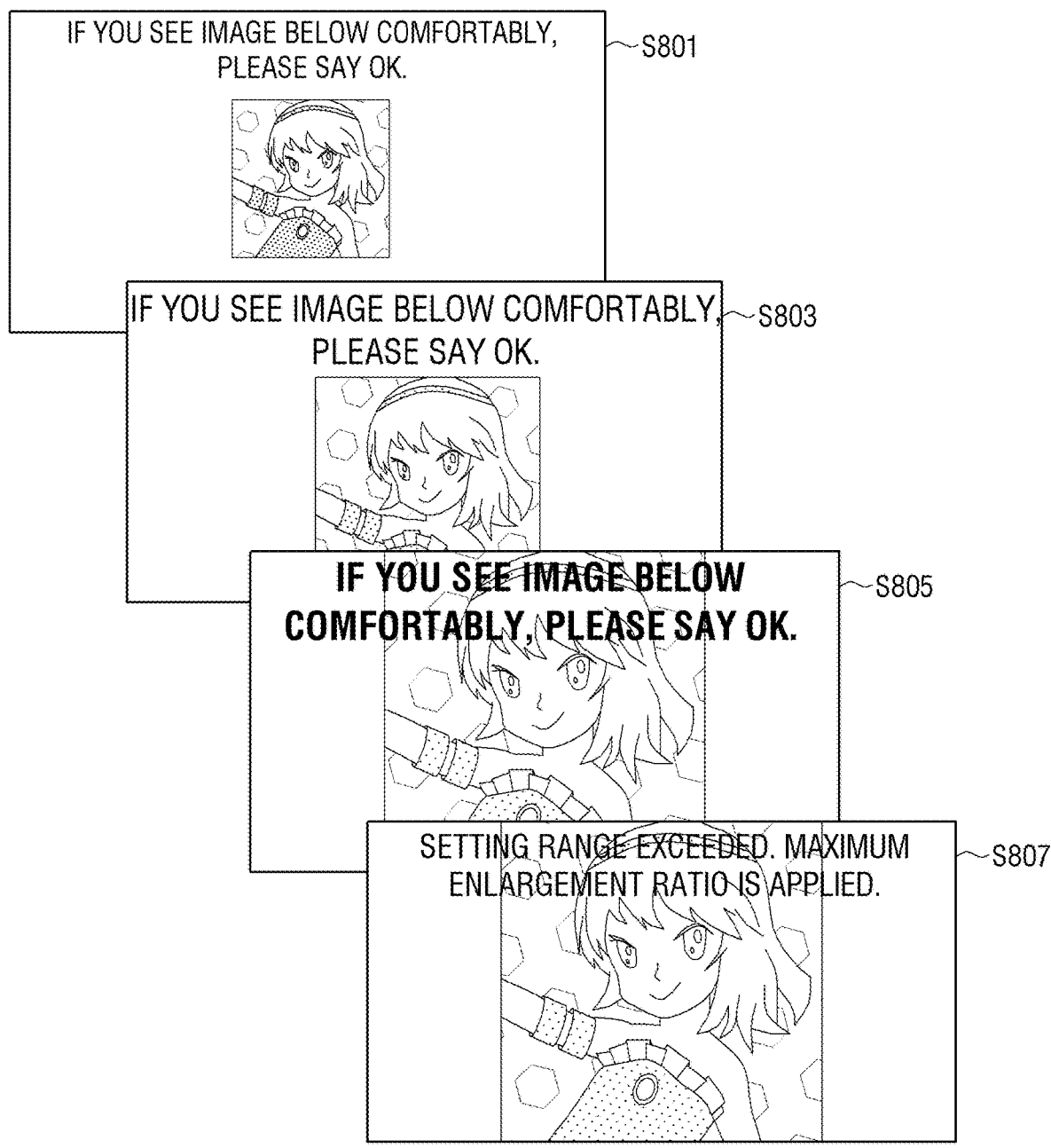
Figure 9:
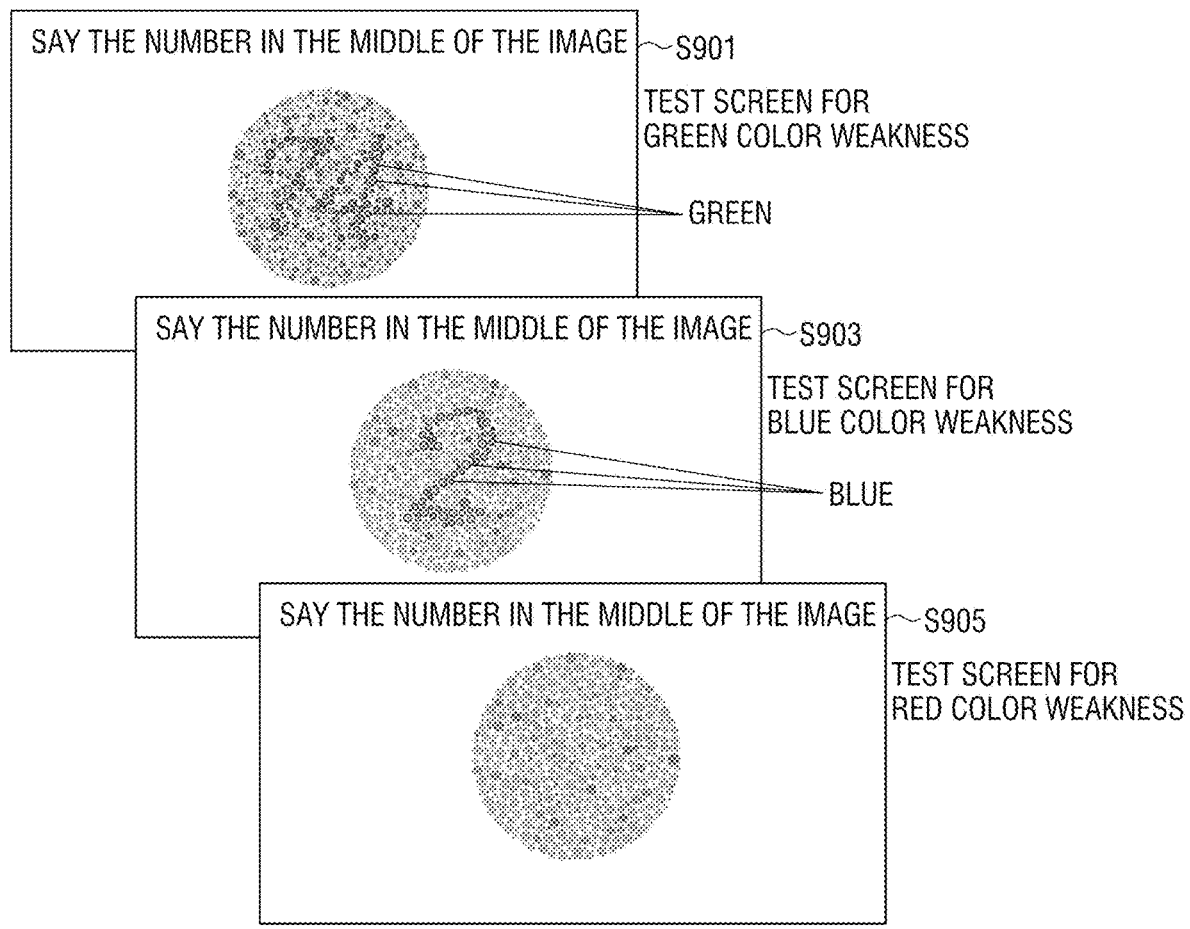

FIGS. 7 to 9 illustrate examples of a visual test screen according to an exemplary embodiment.

Figure 10:
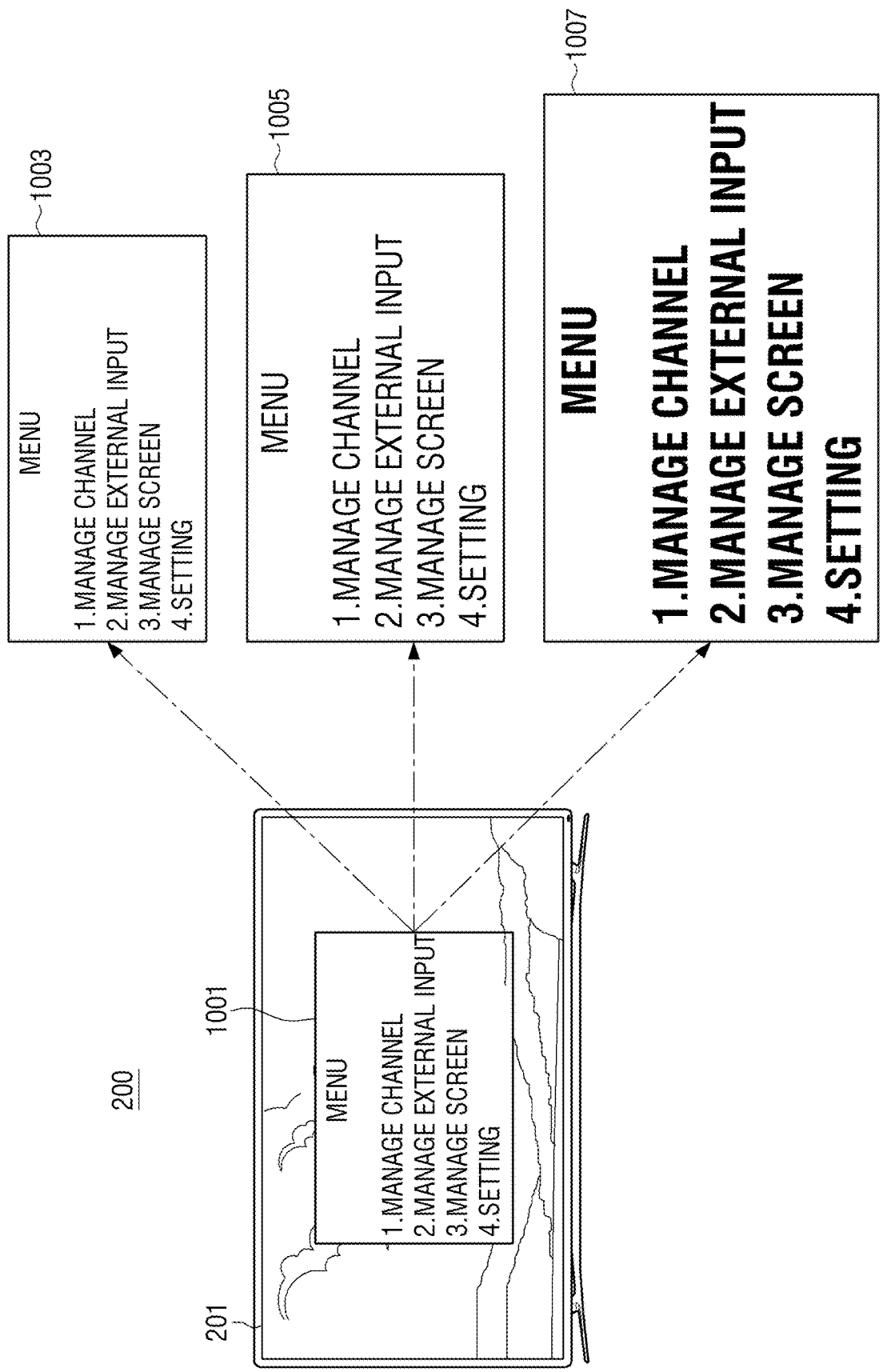
FIG. 10 illustrates an example of setting a UI in a display apparatus according to an exemplary embodiment.

FIG. 10 illustrates an example of setting a UI in a display apparatus according to an exemplary embodiment.

Figure 11:
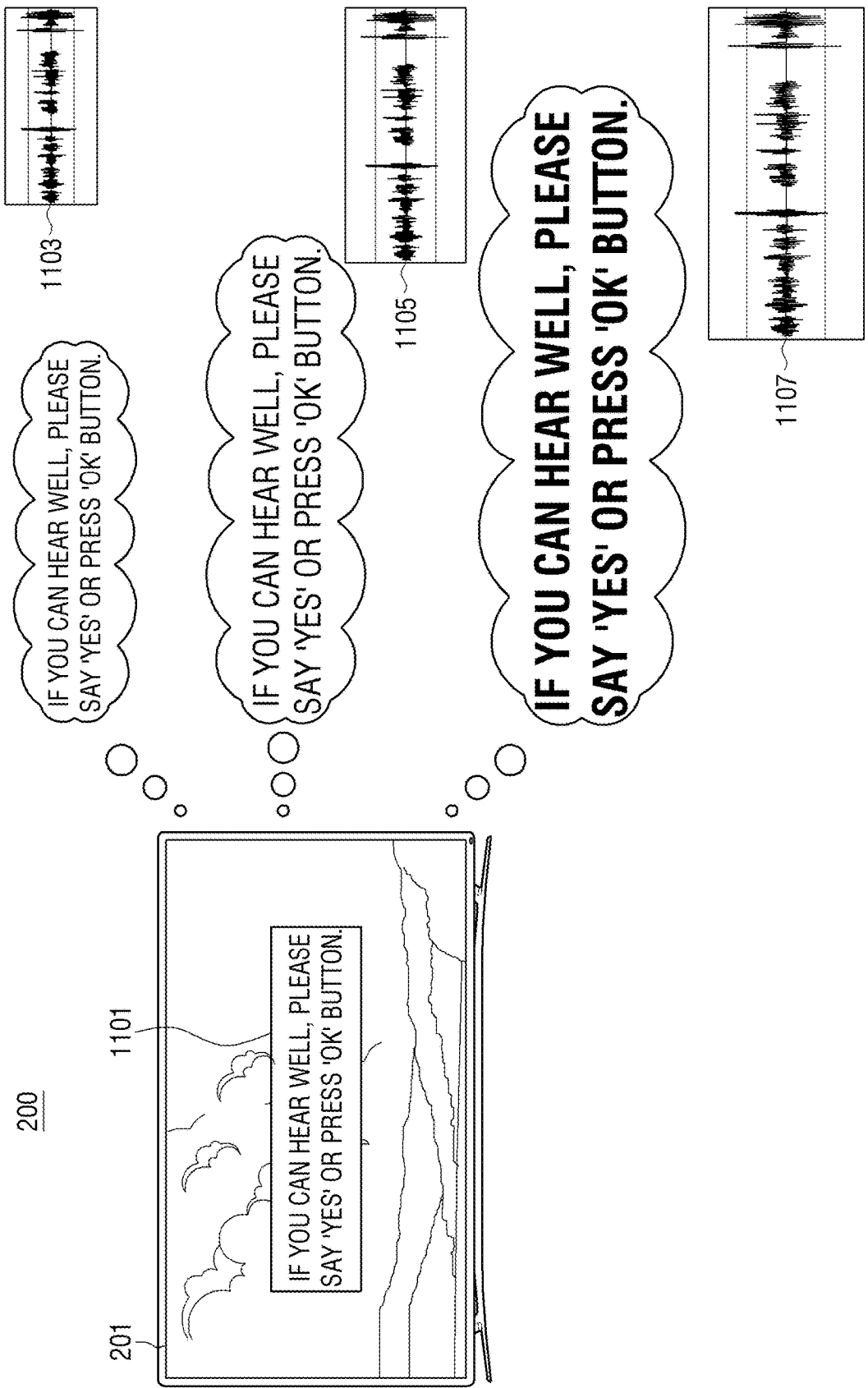
FIGS. 11 to 13 illustrate examples of an auditory test voice signal according to an exemplary embodiment.
Figure 12:
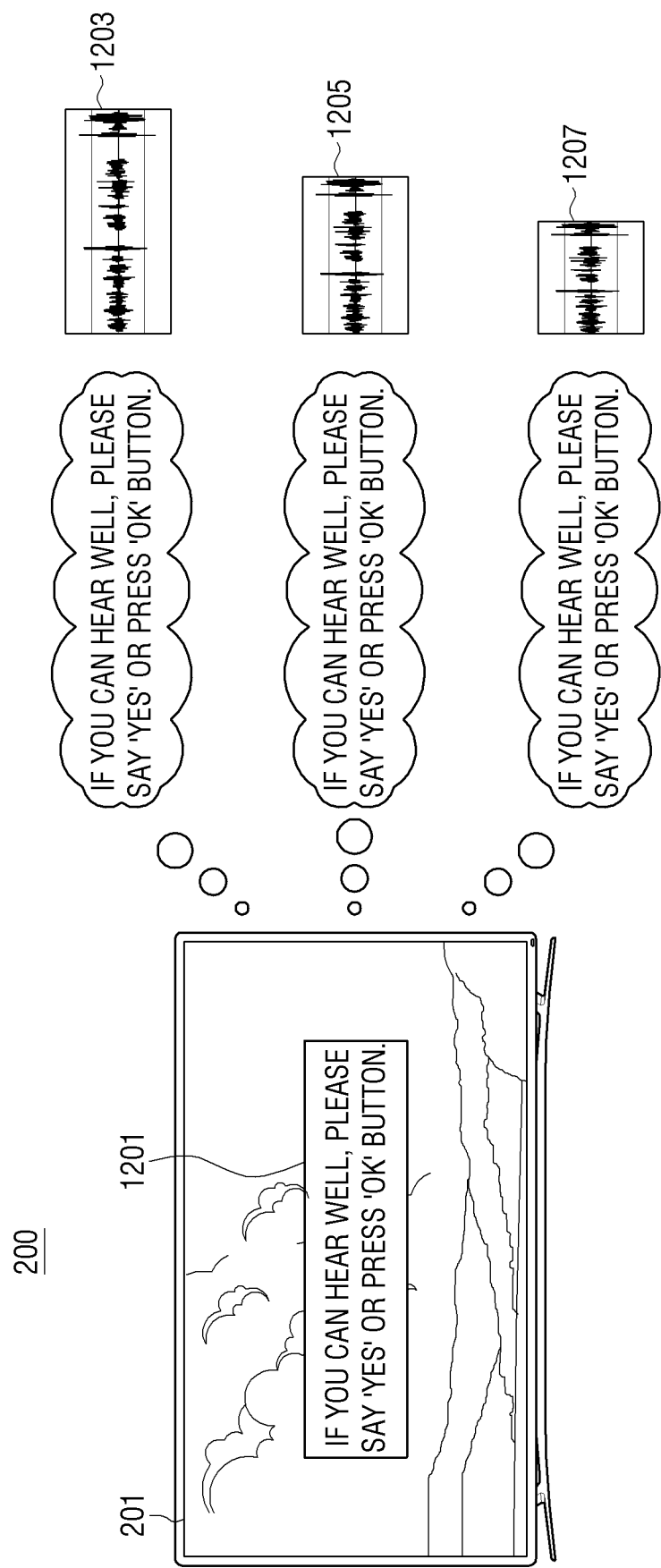
Figure 13:
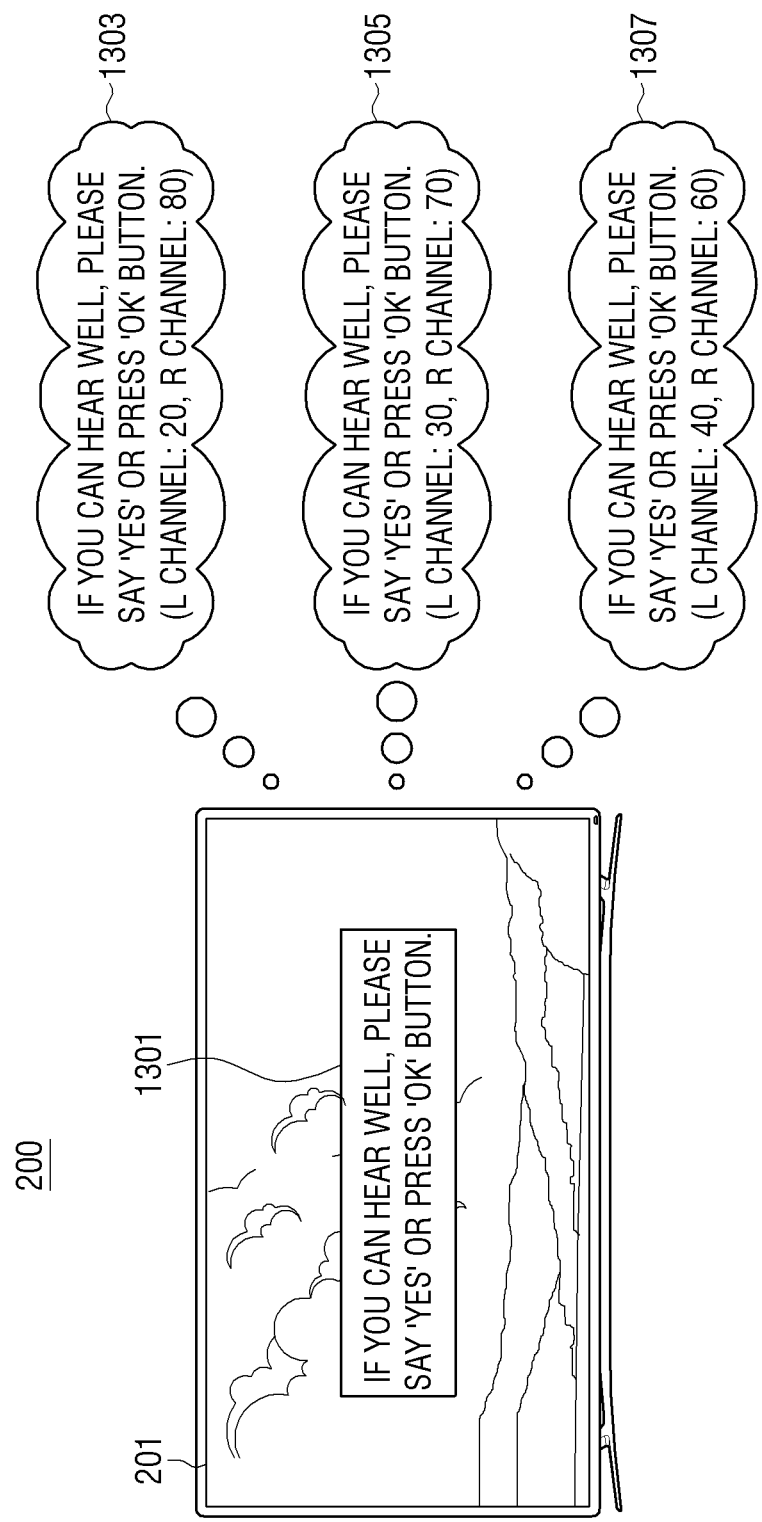

FIGS. 11 to 13 illustrate examples of a voice signal for auditory testing according to an exemplary embodiment.

Figure 14:
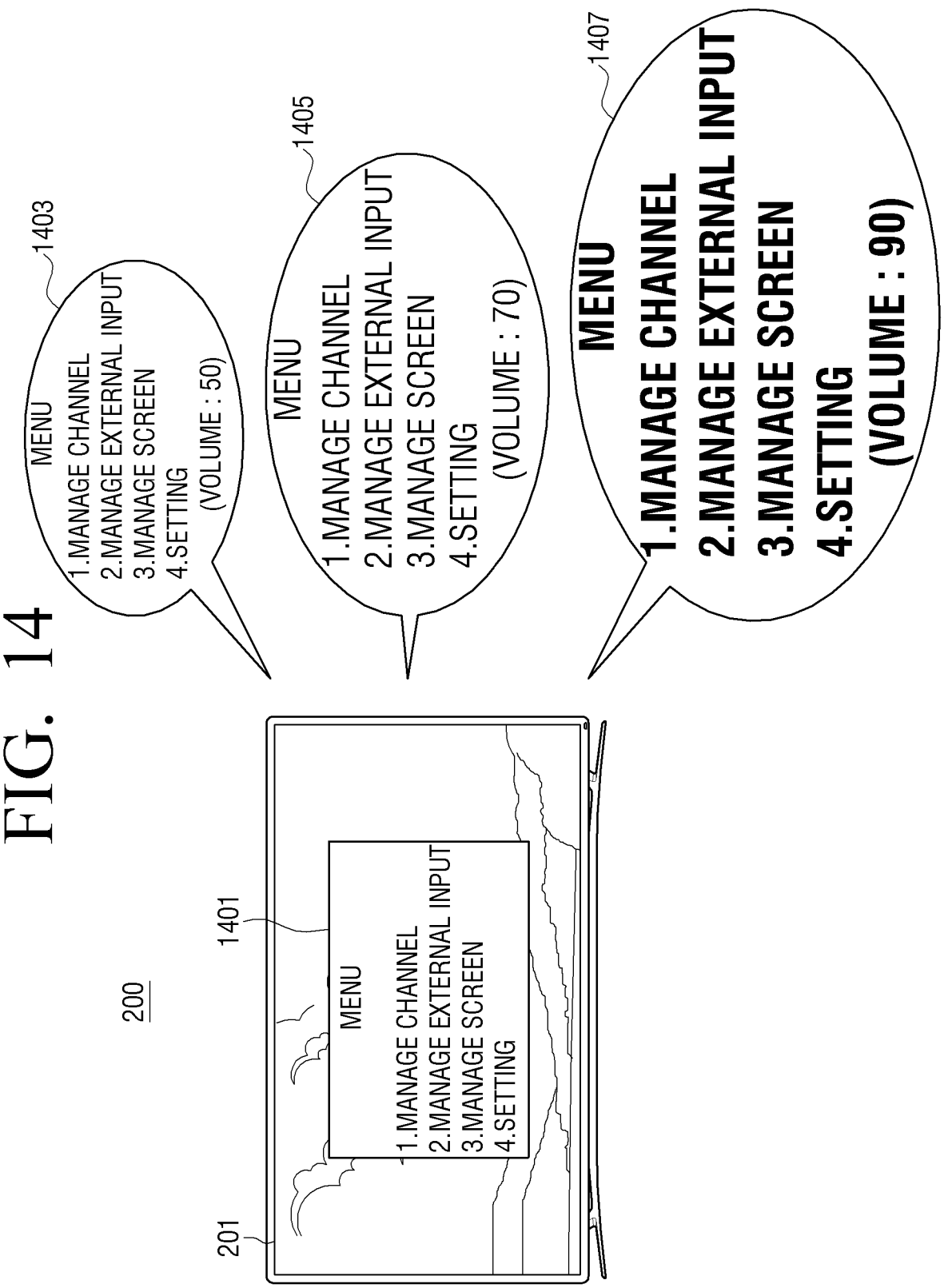
FIG. 14 illustrates an example of setting a voice signal output in a display apparatus according to an exemplary embodiment.

FIG. 14 illustrates an example of setting voice signal output in a display apparatus according to an exemplary embodiment.

For convenience of explanation, the description will be provided with reference to FIGS. 7 to 14.

Referring to FIG. 4, the display apparatus performs at least one of an operation of displaying a visual test screen and an operation of outputting an auditory test voice signal in a display in the step of S401.

The visual test screen may be a screen in which the size of the object included in the screen changes sequentially.

FIG. 7 illustrates screens 701, 703, 705 in which the size of texts on the screen enlarges gradually. The display apparatus may sequentially display the first screen 701, the second screen 703 and the third screen 705 in which the size of the texts enlarges gradually.

FIG. 8 sequentially illustrates screens 801, 803, 805 in which the size of an image including a face of a person on the screen enlarges gradually. The display apparatus may sequentially display the fourth screen 801, the fifth screen 803 and the sixth screen 805 in which the size of the image enlarges gradually.

In addition, the visual test screen may include an image for color weakness test.

FIG. 9 illustrates the seventh screen 901, the eighth screen 903 and the ninth screen 905. The seventh screen 901 may be a test screen for a person with green color weakness. The eighth screen 903 may be a test screen for a person with blue color weakness. The ninth screen 905 may be a test screen for a person with red color weakness. The display apparatus may display the seventh screen 901, the eighth screen 903 and the ninth screen 905 sequentially.

The voice signal for auditory test may be a signal for changing one of the volume, pitch and left-right balance of the voice signal sequentially.

FIG. 11 illustrates an example in which the volume of the voice signal increases sequentially. The volume may correspond to the amplitude, and the larger the amplitude, the greater the volume.

The display apparatus may output the first signal 1103, the second signal 1105 and the third signal 1107 sequentially. For example, the volume of the voice signal may increase in the order of the first signal 1103, the second signal 1105 and the third signal 1107.

FIG. 12 illustrates an example in which the pitch of the voice signal is increased and outputted sequentially. The pitch may correspond to the frequency, and the greater the frequency the higher the pitch.

The display apparatus may output the fourth signal 1203, the fifth signal 1205 and the sixth signal 1207 sequentially. In other words, the display apparatus may output the voice signal while gradually increasing the frequency of the voice signal. For example, the frequency of the voice signal may increase in the order of the fourth signal 1203, the fifth signal 1205 and the sixth signal 1207.

FIG. 13 illustrates an example in which the left-right balance of the voice signal is increased and outputted sequentially. The display apparatus may output the seventh signal 1303, the eighth signal 1305 and the ninth signal 1307 sequentially. In other words, the display apparatus may output the voice signal while changing the left-right balance of the voice signal sequentially.

In step S403, the display apparatus receives a user input while the above operation is performed.

Referring to FIGS. 7 to 13, for example, the display apparatus may receive a user input while the first screen 701 is displayed. If a user input is received, the display apparatus may determine the disability degree and disability classification of the user based on the user input in step S405.

For example, if a user input is received while the first screen 701 is displayed, the display apparatus may determine the disability degree and the disability classification of the user as 'mild visual impairment.'

The display apparatus may display the second screen 703, and if a user input is received while the second screen 703 is displayed, the display apparatus may determine the disability degree and the disability classification of the user as 'mild visual impairment.'

If a user input is received while the third screen 705 is displayed, the display apparatus may determine the disability degree and the disability classification of the user as 'severe visual impairment.'

As described above, the display apparatus may display the first screen 701, the second screen 703, the third screen 705, the fourth screen 801, the fifth screen 803, the sixth screen 805, the seventh screen 901, the eighth screen 903, and the ninth screen 905 sequentially, and if a user input is received, determine whether it is 'mild visual impairment' or 'severe visual impairment' based on the user input.

In another example, if a user input is received while the first signal 1103 is output, the display apparatus may determine that it is 'mild hearing impairment.'

If a user input is received while the second signal 1105 is output, the display apparatus may determine that it is 'mild hearing impairment.'

If a user input is received while the third signal 1107 is output, the display apparatus may determine that it is 'sever hearing impairment.'

As described above, the display apparatus may output the first signal 1103, the second signal 1105, the third signal 1107, the fourth signal 1203, the fifth signal 1205, the sixth signal 1207, the seventh signal 1303, the eighth signal 1305, and the ninth signal 1307 sequentially, and if a user input is received, determine whether it is 'mild hearing impairment' or 'severe hearing impairment' based on the user input.

The display apparatus may set a UI or set voice signal output based on the determined disability degree and disability classification in step S407.

FIG. 10 illustrates that a UI 1001 is displayed on the screen 201 of the display apparatus 200. The display apparatus may select one of a UI 1003, a UI 1005 and a UI 1007 based on the disability degree and disability classification of the user and display the selected UI on the screen 201.

For example, if it is determined that the user has 'mild visual impairment', the display apparatus 200 may display the UI 1003 or the UI 1005 on the screen 201. If it is determined that the user has 'sever visual impairment', the display apparatus 200 may display the UI 1007 on the screen 201. As described above, the display apparatus may change the size of a UI according to the disability degree and the disability classification of the user and display the UI on the screen 201.

FIG. 14 illustrates that a UI 1401 is displayed on the screen 201 of the display apparatus 200 and voice signals 1403, 1405, 1407 according to the volume are output from the display apparatus 200.

The voice signal 1403 indicates that the UI 1401 is output at 'volume 50.'

The voice signal 1405 indicates that the UI 1401 is output at 'volume 70.'

The voice signal 1407 indicates that the UI 1401 is output at 'volume 90.'

The display apparatus may select one of a voice signal 1403, a voice signal 1405 and a voice signal 1407 based on the disability degree and disability classification of the user and set the voice signal output corresponding to the selected signal.

For example, if it is determined that the disability degree and the disability classification of the user is 'mild hearing impairment', the display apparatus may set the voice signal output corresponding to the voice signal 1403 or the voice signal 1405. If it is determined that the disability degree and the disability classification of the user is 'severe hearing impairment', the display apparatus may output the voice signal 1407.

The display apparatus provides information regarding the set UI or the voice signal output through at least one of a visual feedback and an auditory feedback.

For example, the display apparatus 200 may display "UI is set according to the current state" on the screen 201 or provide the corresponding voice guidance while displaying the UI.

Figure 5:
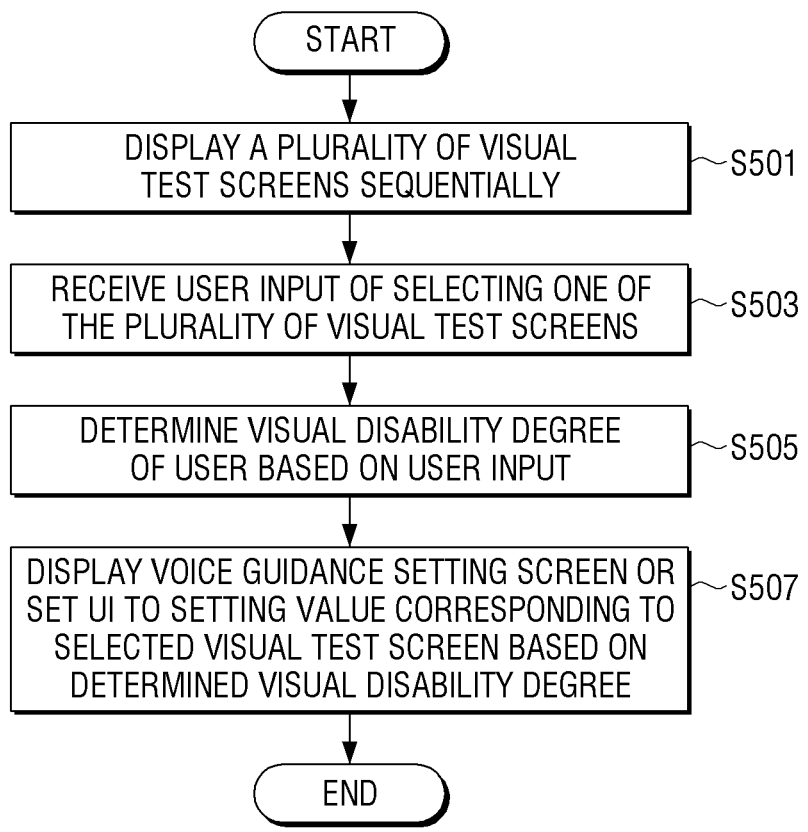
FIG. 5 is a view illustrating a process of displaying a voice guidance setting screen or setting a UI with a setting value corresponding to a visual test screen selected by the user based on a degree of the user's visual impairment by a display apparatus according to an exemplary embodiment.

FIG. 5 illustrates a process in which the display apparatus according to an exemplary embodiment displays a voice guidance setting screen or sets a UI to a setting value corresponding to a visual test screen selected by the user based on the visual impairment degree of the user.

Referring to FIG. 5, the display apparatus displays a plurality of visual test screens sequentially in step S501.

The display apparatus receives a user input of selecting one of the plurality of visual test screens in step S503.

The display apparatus determines a visual impairment degree of the user based on the user input in step S505.

The display apparatus displays a voice guidance setting screen or sets a UI to a setting value corresponding to the selected visual test screen based on the determined visual impairment degree in step S507.

Referring to FIG. 7 as an example, the display apparatus displays the first screen 701, the second screen 703 and the third screen 705 sequentially. If the user utters 'OK' as displayed on the screen while the first screen 701 is displayed, the display apparatus receives the user's voice input and accordingly selects the first screen 701, determines the user's disability degree as 'mild visual impairment', and sets the size of the UI to the font size of the texts displayed on the visual test screen 701 selected by the user.

If the user utters 'OK' as displayed on the screen while the third screen 705 is displayed, the display apparatus determines the user's disability degree as 'severe visual impairment', and sets the size of the UI to the font size of the texts displayed on the visual test screen 705 selected by the user.

Meanwhile, if there is no user input while the third screen 705 is displayed, the display apparatus may display a screen 707 for activating a voice guidance function (hereinafter, referred to as 'a voice guidance setting screen') or activate the voice guidance function.

If it is determined that the user's disability degree is 'severe visual impairment', the display apparatus according to an exemplary embodiment may display the voice guidance setting screen or activate the voice guidance function.

Referring to FIG. 8 as an example, the display apparatus displays the fourth screen 801, the fifth screen 803 and the sixth screen 805 sequentially. If the user utters 'OK' as displayed on the screen while the fourth screen 801 is displayed, the display apparatus receives the user's voice input and accordingly selects the fourth screen 801, determines the user's disability degree as 'mild visual impairment', and sets the font size of the UI to the font size of the texts displayed on the visual test screen 701 selected by the user.

If the user utters 'OK' as displayed on the screen while the sixth screen 805 is displayed, the display apparatus determines the user's disability degree as 'severe visual impairment', and sets the enlargement ratio of the UI to the enlargement ratio corresponding to the visual test screen 805 selected by the user.

Meanwhile, if there is no user input while the third screen 805 is displayed, the display apparatus may display a screen 807 for activating a voice guidance function (hereinafter, referred to as 'a voice guidance setting screen') or activate the voice guidance function.

If it is determined that the user's disability degree is 'severe visual impairment', the display apparatus according to an exemplary embodiment may display the voice guidance setting screen or activate the voice guidance function.

Figure 6:
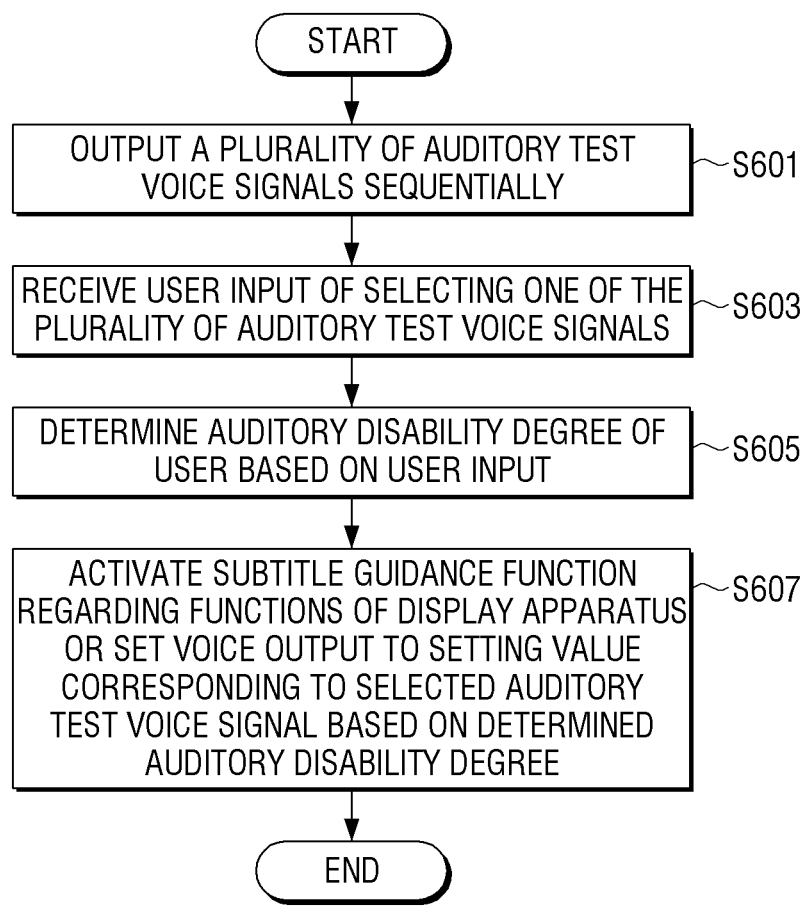
FIG. 6 is a view illustrating a process of activating a subtitle guidance function or setting a voice signal output using a setting value corresponding to an auditory test voice signal selected by a user based on a degree of hearing impairment by a display apparatus according to an exemplary embodiment.

FIG. 6 illustrates a process in which the display apparatus according to an exemplary embodiment activates a subtitle guidance function or sets a voice signal output to a setting value corresponding to an auditory test voice signal selected by the user based on the user's hearing impairment degree.

Referring to FIG. 6, the display apparatus outputs a plurality of auditory test voice signals sequentially in step S601.

The display apparatus receives a user input of selecting one of the plurality of auditory test voice signals in step S603. The user input may be, for example, but is not limited to, a user uttering a particular word.

The display apparatus determines a hearing impairment degree of the user based on the user input in step S605.

The display apparatus activates a subtitle guidance function regarding the functions of the display apparatus or sets a voice signal output to a setting value corresponding to the selected auditory test voice signal based on the determined auditory impairment degree in step S607.

Referring to FIG. 11 as an example, the display apparatus outputs the first voice signal 1103, the second voice signal 1105 and the third voice signal 1107 sequentially. If the user utters 'yes' as it is displayed on the screen or as it sounds while the first voice signal 1103 is output, the display apparatus receives the user's voice input and accordingly selects the first voice signal 1103, determines the user's disability degree as 'mild hearing impairment', and sets the volume of the voice signal to correspond to the volume of the auditory test voice signal 1103 selected by the user.

If the user utters 'yes' as it is displayed on the screen while the third voice signal 1107 is output, the display apparatus determines the user's disability degree as 'severe hearing impairment' and sets the volume of the voice signal to correspond to the volume of the auditory test voice signal 1107 selected by the user.

Meanwhile, if no user input is received while the third voice signal 1107 is output, the display apparatus may determine the user's disability degree as 'severe hearing impairment' and activate a subtitle guidance function.

The functions that the display apparatus performs according to the disability degree and disability classification are not limited to the above examples, which will be described with an example of FIG. 15.

FIG. 15 illustrates an example of functions that can be supported by the display apparatus based on the disability degree and classification of the user according to an exemplary embodiment.

Referring to FIG. 15, if it is determined that the user disability degree is 'mild visual impairment', the display apparatus may perform a function included in a category 1501.

If it is determined that the user disability degree is 'severe visual impairment', the display apparatus may perform a function included in a category 1503.

If it is determined that the user disability degree is 'mild hearing impairment', the display apparatus may perform a function included in a category 1505.

If it is determined that the user disability degree is 'severe hearing impairment', the display apparatus may perform a function included in a category 1507.

If it is determined that the user disability degree is 'reading impairment (dyslexia)', the display apparatus may perform a function included in a category 1509.

If it is determined that the user disability degree is 'hearing comprehension impairment', the display apparatus may perform a function included in a category 1511.

If it is determined that the user has 'physical disability', the display apparatus may perform a function included in a category 1513.

If it is determined that the user has 'color weakness', the display apparatus may perform a function included in a category 1515.

The methods according to the above various embodiments may be implemented to be program command format that can be run through the various computing means, and recorded on a computer readable medium. The computer readable medium may include program commands, data files, and data structures either alone or in combination. For example, the computer-readable medium may be stored in a volatile or non-volatile storage device such as a ROM, a memory such as a RAM, a memory chip, and a device or an integrated circuit, or a storage medium which may be read with a machine (for example, computer processing unit (CPU)) simultaneously with being optically or magnetically recorded like a CD, a DVD, a magnetic disk, a magnetic tape, or the like, regardless of whether it is deleted or recorded again. The memory, which may be included in a mobile terminal, may be one example of a storage medium which may be read with programs including instructions implementing the exemplary embodiments or a machine appropriate to store the programs. The program commands recorded in the recording medium may be especially designed and constituted for the present disclosure or be known to those skilled in a field of computer software.

Although exemplary embodiments have been shown and described, it will be appreciated by those skilled in the art that changes may be made to these exemplary embodiments without departing from the principles and spirit of the present disclosure. Accordingly, the scope of the present invention is not construed as being limited to the described exemplary embodiments, but is defined by the appended claims as well as equivalents thereto.

What is claimed is:

1. A display apparatus, comprising:
an input unit comprising a circuitry;
a speaker;
a display; and
a processor configured to:
control the display to display visual test screens sequentially by changing a size of an object included in each of the visual test screens,
based on a user input being received through the input unit while a visual test screen from among the visual test screens is displayed, identify a degree of impairment of a user and set an enlargement ratio of a User Interface (UI) to correspond to the degree of impairment of the user based on a size of the object included in the visual test screen and control the display to display the UI, and
based on a user input not being received through the input unit while a last visual test screen among the visual test screens is displayed, set the enlargement ratio of the UI to a maximum enlargement ratio of the UI and control the display to display a screen for activating a voice guidance function.

2. The apparatus as claimed in claim 1, wherein the processor provides information regarding the set UI as a visual feedback and an auditory feedback.

3. The apparatus as claimed in claim 1, wherein the UI setting comprises changing at least one of size, color and high-contrast of a UI displayed on the display.

4. The apparatus as claimed in claim 1, wherein the object includes an image including a face of a person, and
wherein the processor controls the display to display the face of the person at a center of a screen.

5. The apparatus as claimed in claim 1, wherein each of the visual test screens includes an image for color weakness test.

6. The apparatus as claimed in claim 1,
wherein the processor is further configured to control the speaker to output an auditory test voice signal;
wherein the auditory test voice signal is output by changing at least one of volume, pitch and left/right balance of the auditory test voice signal.

7. The apparatus as claimed in claim 1, wherein the outputting the voice signal further comprises changing at least one of volume, pitch and left/right balance of the output voice signal.

8. A display apparatus, comprising:
an input unit comprising a circuitry;
a speaker;
a display; and
a processor configured to:
sequentially output a plurality of auditory test voice signals via the speaker,
based on a user input being received while the plurality of auditory test voice signals are output, determine a degree of hearing impairment of a user and set a voice signal output to correspond to the degree of hearing impairment of the user, and
based on a user input not being received while a last auditory test voice signal among the plurality of auditory test voice signals is output, activate a subtitle guidance function of the display apparatus.

9. A method for controlling a display apparatus, comprising:
displaying visual test screens sequentially by changing a size of an object included in each of the visual test screens; and
setting an enlargement ratio of a User Interface (UI) to a different enlargement ratio based on whether a user input is received while a last visual test screen among the visual test screens is displayed,
wherein based on a user input being received while a visual test screen from among the visual test screens is displayed, a degree of impairment of a user is identified, the enlargement ratio of the UI is set to correspond to the degree of impairment of the user based on a size of the object included in the visual test screen and the set UI is displayed, and
wherein based on a user input not being received while the last visual test screen among the visual test screens is displayed, the enlargement ratio of the UI is set to a maximum enlargement ratio of the UI and a screen for activating a voice guidance function is displayed.

10. The method as claimed in claim 9, further comprising:
providing information regarding the set UI as a visual feedback.

11. The method as claimed in claim 9, wherein the UI setting comprises changing at least one of size, color and high-contrast of a UI displayed on the display.

12. The method as claimed in claim 9, wherein the object includes an image including a face of a person, and
wherein the displaying the visual test screens comprises displaying the face of the person at a center of a screen.

13. The method as claimed in claim 9, wherein each of the visual test screens includes an image for color weakness test.

14. The method as claimed in claim 9, further comprising:
outputting an auditory test voice signal;
wherein the auditory test voice signal is output by changing at least one of volume, pitch and left/right balance of the voice signal.

15. The method as claimed in claim 9, further comprising outputting a voice signal, wherein the outputting the voice signal further comprises changing at least one of volume, pitch and left/right balance of the output voice signal.

* * * * *